US012414913B1

(12) United States Patent
Dave et al.

(10) Patent No.: US 12,414,913 B1
(45) Date of Patent: Sep. 16, 2025

(54) IMPLANTABLE DEVICE HAVING PISTON DISPLACEMENT MONITORING

(71) Applicant: MantaMedTech LLC, Newark, DE (US)

(72) Inventors: Raju S. Dave, Gaithersburg, MD (US); Xing Su, Santa Clara, CA (US); Himanshu Verma, McLean, VA (US); Palamadai Venkatraman, Edison, NJ (US)

(73) Assignee: MantaMedTech LLC

( * ) Notice: Subject to any disclaimer, the term of this patent is extended or adjusted under 35 U.S.C. 154(b) by 0 days.

(21) Appl. No.: 19/006,316

(22) Filed: Dec. 31, 2024

(51) Int. Cl.
    *A61K 9/00* (2006.01)
    *A61M 5/168* (2006.01)

(52) U.S. Cl.
    CPC ....... *A61K 9/0004* (2013.01); *A61M 5/16813* (2013.01); *A61M 2205/18* (2013.01); *A61M 2205/3306* (2013.01); *A61M 2205/3317* (2013.01); *A61M 2205/3344* (2013.01); *A61M 2205/3375* (2013.01)

(58) Field of Classification Search
    CPC ............ A61K 9/0004; A61M 5/16813; A61M 2205/18; A61M 2205/3306; A61M 2205/3317; A61M 2205/3344; A61M 2205/3375
See application file for complete search history.

(56) References Cited

U.S. PATENT DOCUMENTS

| | | | |
|---|---|---|---|
| 4,714,762 A * | 12/1987 | Hoefle | C07D 471/04 514/394 |
| 6,224,550 B1 | 5/2001 | Ellingsen | |
| 2008/0091176 A1* | 4/2008 | Alessi | A61M 5/14276 604/892.1 |
| 2011/0196189 A1 | 8/2011 | Milbocker | |
| 2015/0105751 A1 | 4/2015 | Uhland et al. | |
| 2018/0338904 A1 | 11/2018 | Uhland et al. | |
| 2023/0201549 A1 | 6/2023 | Davey | |
| 2024/0376809 A1* | 11/2024 | Hurst | E21B 43/129 |

OTHER PUBLICATIONS

Search report and Written opinion issued for PCT/US2025/062373, mailed on Mar. 26, 2025, 17 pages.

* cited by examiner

*Primary Examiner* — Bhisma Mehta
*Assistant Examiner* — Haden Matthew Ritchie
(74) *Attorney, Agent, or Firm* — Raj S. Dave; Davé Law Group, LLC

(57) ABSTRACT

An embodiment relates to an active implantable medical device (AIMD), comprising: a permeability module that allows ingress flow of a fluid to an osmotic agent chamber and generates osmotic pressure; a piston that moves longitudinally within the active implantable medical device (AIMD) in response to the osmotic pressure; a drug chamber that comprises a drug and a valve module to allow one-way flow of the drug from the drug chamber to outside the active implantable medical device (AIMD); a sensor module that measures a displacement of the piston in real-time; and an electronic module that communicates a signal to the valve module to control the valve module and regulate the one-way flow of the drug based on the displacement of the piston.

20 Claims, 15 Drawing Sheets

IMPLANTABLE DEVICE HAVING PISTON DISPLACEMENT MONITORING

CROSS REFERENCE TO RELATED APPLICATIONS

This application claims priority from the following applications shown in the Table below, which are incorporated by reference herein in its entirety.

| U.S. Pat. application Ser. Nos. | Filing Date | Title of the Invention |
|---|---|---|
| 63/617,054 | 2 JAN. 2024 | PERSONALIZED DRUG DOSING |
| 63/617,057 | 2 JAN. 2024 | INNOVATIVE IMPLANTABLE DEVICE USING DOSING CONTROL TO PREVENT MEDICATION ERRORS |
| 63/617,754 | 4 JAN. 2024 | IMPLANTABLE DEVICE FOR PRECISION DOSING |
| 63/566,519 | 18 MAR. 2024 | IMPLANTABLE DRUG DELIVERY DEVICE |
| 63/574,330 | 4 APR. 2024 | INNOVATIVE IMPLANTABLE DEVICE USING DOSING CONTROL TO PREVENT MEDICATION ERRORS |
| 63/661,654 | 19 JUN. 2024 | DEVICE BASED TREATMENTS FOR SUBSTANCE USE DISORDERS |
| 18,781,451 | 23 JUL. 2024 | ARTIFICIAL INTELLIGENCE BASED IMPLANTABLE DRUG DELIVERY SYSTEM |
| 63/689,805 | 2 SEP. 2024 | IMPLANTABLE DEVICE FOR DRUG DELIVERY |
| 63/713,149 | 29 OCT. 2024 | AUTOMATED OVERDOSE RESPONSE SYSTEM FOR ON-DEMAND NALOXONE DELIVERY |

TECHNICAL FIELD

This disclosure relates to active implantation medical device (AIMD), and more specifically relates to non-pressure sensor based piston displacement monitoring in active implantation medical device (AIMD) to provide adjustable dose.

BACKGROUND

Medication adherence remains a significant challenge in healthcare, especially among patients with chronic conditions and the elderly, who often manage multiple medications. Poor adherence leads to worsened health outcomes, including increased hospitalization and mortality rates, while also contributing to high healthcare costs. This problem is further exacerbated by cognitive impairments, negative attitudes toward treatment, and substance abuse. Additionally, the opioid crisis has highlighted the need for more effective drug management strategies to prevent overdose and ensure proper medication administration. Traditional methods of drug delivery often fail to provide accurate, personalized dosages, leaving a gap in managing complex conditions effectively.

Current drug delivery systems often rely on simple mechanisms that do not offer the precision required to adjust dosages according to a patient's specific needs. In particular, many systems depend on mechanical components such as pistons, which regulate the flow of drugs by responding to osmotic pressure. However, without accurate and real-time measurement of piston displacement, it becomes difficult to ensure the correct amount of medication is delivered. This limitation results in the potential for over- or under-delivery of drugs, which could lead to adverse effects, ineffective treatment, or complications in patient care. Therefore, addressing the accuracy and control of drug delivery is critical to improving health outcomes.

BRIEF SUMMARY

The following paragraphs present a summary to provide a basic understanding of one or more embodiments described herein. This summary is not intended to identify key or critical elements or delineate any scope of the different embodiments and/or any scope of the claims. The sole purpose of the summary is to present some concepts in a simplified form as a prelude to the more detailed description presented herein.

Embodiments relate to an active implantable medical device (AIMD) comprising a permeability module, which allows body fluid to enter the device through a semi-permeable membrane. This fluid flows into an osmotic agent chamber, where it generates osmotic pressure that drives the movement of a piston within the device. The piston moves longitudinally in response to this osmotic pressure, enabling the drug release process.

The AIMD comprises a drug chamber that comprises the drug to be delivered and a valve module that controls the one-way flow of the drug from the chamber to the outside of the device. The valve module ensures that the drug flows in the intended direction, maintaining the integrity of the controlled release mechanism. The AIMD comprises a sensor module incorporated to measure the displacement of the piston in real-time. The sensor module provides the displacement data regarding the position of the piston, ensuring that the drug release is synchronized with its movement.

The electronic module communicates a signal to the valve module based on the displacement data from the sensor module. This enables the electronic module to regulate the valve and control the drug flow in response to the piston's movement. The AIMD is designed to function with a tubular structure, making it suitable for subcutaneous implantation, where it can continuously release the drug over an extended period. Throughout its operation, the AIMD ensures that osmotic pressure drives the piston's movement, while the sensor monitors the piston's displacement to ensure precise drug delivery. A communication network connects all the modules, ensuring synchronized operation of the device components. By continuously monitoring and adjusting the piston's movement, the device maintains an accurate, controlled release of the drug, responding to changes in osmotic pressure and maintaining the intended therapeutic effect.

In an aspect, an active implantable medical device (AIMD) is described. The active implantable medical device (AIMD) comprises: a permeability module that allows ingress flow of a fluid to an osmotic agent chamber and generates osmotic pressure; a piston that moves longitudinally within the active implantable medical device (AIMD) in response to the osmotic pressure; a drug chamber that comprises a drug and a valve module to allow one-way flow of the drug from the drug chamber to outside the active implantable medical device (AIMD); a sensor module that measures a displacement of the piston in real-time; and an electronic module that communicates a signal to the valve module to control the valve module and regulate the one-way flow of the drug based on the displacement of the piston.

The sensor module comprises one or more non-pressure-based sensors, including but not limited to at least one of a Linear Variable Differential Transformer (LVDT), a magnetic position sensor, an optical sensor, an ultrasonic sensor, a capacitive displacement sensor, an inductive displacement sensor, a capacitive proximity sensor, an inductive proximity sensor, an inductive impedance sensor, a capacitive impedance sensor, an eddy current based impedance sensor, and a resonance-based impedance sensor.

In some embodiments, the active implantable medical device (AIMD) is configured to be implanted subcutaneously in a subject. The subject may be a living organism. In some embodiments, the living organism may be a mammal. The mammal may be a human being.

In some embodiments, the electronic module comprises a microcontroller. The AIMD may comprise a power module, which comprises a power source to power one or more components of the AIMD.

In some embodiments, the piston operates at a constant speed or a variable speed. In some embodiments, the displacement of the piston may be a linear displacement. In other embodiments, the displacement may be a rectilinear displacement. The displacement of the piston may be proportional to an amount of discharge of the drug. In some embodiments, the displacement of the piston and the osmotic pressure within the permeability module may have a co-relation. The piston may be one of a metallic piston or a non-metallic piston.

In some embodiments, the drug chamber of the AIMD comprises a threshold displacement limit. The threshold displacement limit may correspond to a prescribed drug quantity. The prescribed drug quantity may be a maximum drug quantity intended for the subject.

In some embodiments, the AIMD is configured to discharge a fixed dose of the drug. In other embodiments, the AIMD is configured to discharge a variable dose of the drug. The amount of drug released in a single shot of the AIMD may equal the distance travelled by the piston times the cross sectional area of the AIMD. In some embodiments, a dose-to-dose drug ejection variation from the AIMD may be less than ±25% by a predetermined volume. In some embodiments, the dose-to-dose drug ejection variation may be ±10% or less by the predetermined volume.

In some embodiments, the sensor module measures the displacement of the piston through a non-contact measurement. In some embodiments, the sensor module may measure the displacement of the piston through a contact measurement.

In some embodiments, the valve module comprises a flow switch. The flow switch may comprise an ON-OFF flow switch. The ON-OFF flow switch may comprise a relief valve, a push rod, and a stepper motor. In some embodiments, the AIMD is activated to start operation either manually or automatically.

In another aspect, a method is described. The method comprises the steps of: measuring displacement of a piston inside an active implantable medical device (AIMD) using one or more sensors; communicating displacement data to an electronic module; generating a signal based on the displacement data using the electronic module; and controlling a valve module and regulating a discharge rate of a drug based on the received signal using the electronic module and the displacement of the piston correspond to the discharge rate of the drug from the active implantable medical device (AIMD).

In some embodiments, the displacement of the piston as a function of osmotic pressure w is calculated as $$\text{DISPLACEMENT } D = \frac{2CRT}{A}\left(\frac{1}{\pi 2} - \frac{1}{\pi 1}\right) \qquad \text{Equation (I)}$$

where R is ideal gas constant, T is temperature, C is concentration of an osmotic agent, A is cross sectional area, $\pi 1$ is initial osmotic pressure and $\pi_2$ is current osmotic pressure.

The active implantable medical device (AIMD) may be configured to use machine learning to adjust a drug dose as per need of a user.

In some embodiments, the one or more sensors are external to the active implantable medical device (AIMD). In some embodiments, the one or more sensors are internal to the active implantable medical device (AIMD).

In another aspect, a system is described. The system comprises one or more sensors configured to measure a displacement of a piston and provide displacement data during real-time operation of an active implantable medical device (AIMD), an external sensor placed outside the active implantable medical device (AIMD) configured to provide a physiological parameter of a user having the active implantable medical device (AIMD), an artificial intelligence (AI) system configured to receive and analyze the displacement data and the physiological parameter to predict a body response of the user using the active implantable medical device (AIMD); and a smart alert system, the smart alert system in communication with the active implantable medical device (AIMD) and the external sensor configured to proactively send out a signal for help based on a predicted body response by the AI system.

In some embodiments, the AI system, and the active implantable medical device (AIMD) are in wireless communication with one another.

In some embodiments, the AI system is configured to store monitored inputs from the active implantable medical device (AIMD) and the physiological parameter of the user. The AI system may implement one or more of predictive learning, machine learning, automated planning and scheduling, machine perception, computer vision, and affective computing to predict the body response of the user.

In some embodiments, the AI system is configured to access a medication schedule and to send a signal to administer medicine based on the medication schedule to the active implantable medical device (AIMD). The system may be configured to update a machine learning model based on a physical parameter of the active implantable medical device (AIMD) and a generated physiological condition of the user on a real-time basis. In some embodiments, the system is configured to adjust a drug dosing schedule based on a predicted outcome of AI.

In some embodiments, the AI system is configured to predict a future working condition of the active implantable medical device (AIMD) and notify the user or a healthcare provider if the future working condition of the active implantable medical device (AIMD) is not within ±15% value of the corresponding expected value of the active implantable medical device (AIMD). In some embodiments, the future working condition comprises the displacement of the piston and an osmotic pressure of the active implantable medical device (AIMD).

In another aspect, a non-transitory computer readable storage medium is described. The non-transitory computer readable storage medium comprising a sequence of instructions, which when executed by a processor causes: measuring displacement of a piston inside an active implantable medical device (AIMD) using one or more sensors; communicating displacement data to an electronic module; generating a signal based on the displacement data using the electronic module; and controlling a valve module and regulating a discharge rate of a drug based on the signal using the electronic module and the displacement of the piston corresponding to the discharge rate of the drug from the active implantable medical device (AIMD).

In some embodiments, the displacement of the piston as a function of osmotic pressure w is calculated as $$\text{DISPLACEMENT } D = \frac{2CRT}{A}\left(\frac{1}{\pi 2} - \frac{1}{\pi 1}\right) \quad \text{Equation (I)}$$

where R is ideal gas constant, T is temperature, C is concentration of an osmotic agent, A is cross sectional area, $\pi 1$ is initial osmotic pressure and $\pi_2$ is current osmotic pressure.

The active implantable medical device (AIMD) may be configured to use machine learning to adjust a drug dose as per need of a user.

In some embodiments, the one or more sensors are external to the active implantable medical device (AIMD). In some embodiments, the one or more sensors are internal to the active implantable medical device (AIMD).

The methods and systems disclosed herein may be implemented by any means necessary for achieving various aspects to perform any of the operations disclosed herein. Other features will be apparent from the accompanying drawings and from the detailed description that follows.

BRIEF DESCRIPTION OF THE FIGURES

These and other aspects of the present disclosure will now be described in more detail, with reference to the appended drawings showing exemplary embodiments of the present disclosure, in which.

Figure 1:
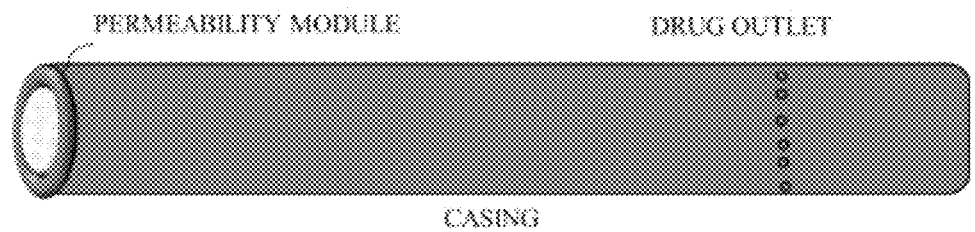
FIG. 1 illustrates an outside view of an active implantable medical device (AIMD) with a permeability module present at one end of said device, according to one or more embodiments.

Other features of the present embodiments will be apparent from the accompanying drawings and from the detailed description that follows.

DETAILED DESCRIPTION

Definitions and General Techniques

For simplicity and clarity of illustration, the drawing figures illustrate the general manner of construction, and descriptions and details of well-known features and techniques may be omitted to avoid unnecessarily obscuring the present disclosure. Additionally, elements in the drawing figures are not necessarily drawn to scale. For example, the dimensions of some of the elements in the figures may be exaggerated relative to other elements to help improve understanding of embodiments of the present disclosure. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the apparatus, methods, and/or articles of manufacture described herein are, for example, capable of operation in other orientations than those illustrated or otherwise described herein.

No element, act, or instruction used herein should be construed as critical or essential unless explicitly described as such. Also, as used herein, the articles "a" and "an" are intended to include items and may be used interchangeably with "one or more." Furthermore, as used herein, the term "set" is intended to include items (e.g., related items, unrelated items, a combination of related items, and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

The terms "couple," "coupled," "couples," "coupling," and the like should be broadly understood and refer to connecting two or more elements mechanically and/or otherwise. Two or more electrical elements may be electrically coupled together, but not be mechanically or otherwise coupled together. Coupling may be for any length of time, e.g., permanent or semi-permanent or only for an instant. "Electrical coupling" and the like should be broadly understood and include electrical coupling of all types. The absence of the word "removably," "removable," and the like near the word "coupled," and the like does not mean that the coupling, etc., in question is or is not removable.

As defined herein, two or more elements are "integral" if they are comprised of the same piece of material. As defined herein, two or more elements are "non-integral" if each is comprised of a different piece of material.

As defined herein, "real-time" can, in some embodiments, be defined with respect to operations carried out as soon as practically possible upon occurrence of a triggering event. A triggering event can include receipt of data necessary to execute a task or to otherwise process information. Because of delays inherent in transmission and/or in computing speeds, the term "real-time" encompasses operations that occur in "near" real-time or somewhat delayed from a triggering event. In a number of embodiments, "real-time" can mean real-time less a time delay for processing (e.g., determining) and/or transmitting data. The particular time delay can vary depending on the type and/or amount of the data, the processing speeds of the hardware, the transmission capability of the communication hardware, the transmission distance, etc. However, in many embodiments, the time delay can be less than approximately one second, two seconds, five seconds, or ten seconds.

The present disclosure may be embodied in other specific forms without departing from its spirit or characteristics. The embodiments described are to be considered in all respects only as illustrative and not restrictive. The scope of the disclosure is, therefore, indicated by the appended claims rather than by the foregoing description. All changes which come within the meaning and range of equivalents of the claims are to be embraced within their scope.

As defined herein, "approximately" can, in some embodiments, mean within plus or minus ten percent of the stated value. In other embodiments, "approximately" can mean within plus or minus five percent of the stated value. In further embodiments, "approximately" can mean within plus or minus three percent of the stated value. In yet other embodiments, "approximately" can mean within plus or minus one percent of the stated value.

Unless otherwise defined herein, scientific and technical terms used in connection with the present disclosure shall have meanings that are commonly understood by those of ordinary skill in the art. Further, unless otherwise required by context, singular terms shall include pluralities and plural terms shall include the singular. Generally, nomenclatures used in connection with, and techniques of, health monitoring described herein are those well-known and commonly used in the art.

The methods and techniques of the present disclosure are generally performed according to conventional methods well-known in the art and as described in various general and more specific references that are cited and discussed throughout the present specification unless otherwise indicated. The nomenclatures used in connection with, and the procedures and techniques of, embodiments herein and other related fields described herein are those well-known and commonly used in the art.

The following terms and phrases, unless otherwise indicated, shall be understood to have the following meanings.

The term "ingress flow" refers to the movement of a fluid into the osmotic agent chamber through the permeability module, driven by osmotic pressure, which generates longitudinal movement of the piston within the active implantable medical device (AIMD).

The term "one-way flow" refers to the controlled movement of the drug from the drug chamber to the outside of the active implantable medical device (AIMD), allowing the drug to flow in only one direction.

The term "medication" refers to a substance or combination of substances or drug used to diagnose, treat, prevent, or alleviate symptoms of a disease or medical condition.

The term "displacement" refers to the movement or shift of the piston within the active implantable medical device (AIMD), typically measured in terms of distance or position.

The term "threshold displacement limit" refers to the specific displacement value of the piston within the active implantable medical device (AIMD) that corresponds to a predefined amount of drug release, typically representing the maximum drug quantity intended to be delivered to a subject.

The term "constant speed" refers to the uniform and unchanging rate at which the piston moves within the active implantable medical device (AIMD) over time. The piston may move at the same speed regardless of external factors, such as changes in osmotic pressure.

The term "variable speed" refers to the rate at which the piston moves within the active implantable medical device (AIMD) that changes over time, often in response to dynamic conditions such as variations in osmotic pressure or the amount of drug to be delivered.

The term "linear displacement" refers to the movement of the piston along a straight path in a specific direction, where the displacement occurs in a single dimension, typically along a straight line, without any deviation or change in direction.

The term "rectilinear displacement" refers to displacement along a straight line, similar to linear displacement. It specifically implies motion along a straight line, without deviation or curvature.

The term "power source" refers to a component that could provide necessary energy to operate the device. Typically, this is a battery housed within the system's case.

The term "microcontroller" (MCU for microcontroller unit) is a small computer on a single metal-oxide-semiconductor (MOS) integrated circuit (IC) chip. A microcontroller contains one or more CPUs (processor cores) along with memory and programmable input/output peripherals. Program memory in the form of ferroelectric Random Access Memory (RAM), Not OR flash (NOR flash) or One-time programmable read-only memory (OTP ROM) is also often included on chips, as well as a small amount of RAM.

In an embodiment, microcontrollers may be designed for embedded applications.

In an embodiment, microcontrollers may comprise various discrete chips.

In an embodiment, microcontrollers may also receive physiological signals sensed by selected electrodes or other sensors via a switch device. In some examples, a microcontroller may receive physiological signals sensed by at least one electrode, which may be used alone or in combination with other electrodes for delivery of medication. Furthermore, a processor may additionally or alternatively receive at least one signal generated by one or more other sensors coupled to a processor via lead or wirelessly, e.g. via a communication module.

The term "microcontroller" may be used interchangeably with terms such as "controller", "processor" or "microprocessor" and the like.

The term "adhesive" is any non-metallic substance applied to one or both surfaces of two separate items that binds them together and resists their separation. Adhesives are also known as glue, cement, mucilage, or paste. There are a large number of adhesive types for various applications. They may be classified in a variety of ways depending on their chemistries (e.g. epoxies, polyurethanes, polyimides), their form (e.g. paste, liquid, film, pellets, tape), their type (e.g. hot melt, reactive hot melt, thermosetting, pressure sensitive, contact, etc.), or their load carrying capability (structural, semi-structural, or non-structural). Any type of adhesive comes under the scope of the disclosure. There are adhesives known in the art based on their functionality, for example, core adhesives add strength to the diaper pad when it is wet, construction adhesives bind the waterproof back sheet to the nonwoven absorbent pads, and elastic adhesives bind legs, waist and lateral panel sheets.

In an embodiment, the disclosure measures a value of a physiological parameter for a subject at a selected state (e.g., state of peak metabolism, state of lowered metabolism, state of rest, etc.), including obtaining, via a device attached to the subject, a value of the physiological parameter of the subject at a particular time-of-day, and applying a time-dependent relationship function to the obtained physiological parameter value via at least one processor to determine a value of the physiological parameter at the selected state.

The term "sensor" is a device, module, machine, or subsystem whose purpose is to detect change in position of piston and send the information to other electronics, frequently a computer processor. A sensor is always used with other electronics.

The term "biosensor" is an analytical device, used for the detection of a chemical substance, that combines a biological component with a physicochemical detector. The sensitive biological element, e.g., tissue, microorganisms, organelles, cell receptors, enzymes, antibodies, nucleic acids, etc., is a biologically derived material or biomimetic component that interacts, binds with, or recognizes the analyte under study. According to one embodiment, all types of biosensors come under the scope of the present disclosure. The biosensor helps in detecting physiological parameters of the body.

The term "semi-permeable membrane" is a type of biological, synthetic or polymeric membrane that allows certain molecules or ions to pass through it by diffusion—or occasionally by more specialized processes of facilitated diffusion, passive transport or active transport. The rate of passage depends on the pressure, concentration, and temperature of the molecules or solutes on either side, as well as the permeability of the membrane to each solute. Depending on the membrane and the solute, permeability may depend on solute size, solubility, properties, or chemistry.

The term "energy storing device" is a device that stores energy, generally referred to as an accumulator or battery. The battery could be a rechargeable battery such as but not limited to Lead-acid battery, Nickel-cadmium battery (NiCd), Nickel-metal hydride battery (NiMH), Lithium-ion battery, Lithium-ion polymer battery. In an embodiment, the battery could be a flow battery.

The term "waterproof safeguards" or "waterproofing agent" or the like refers to materials such as but not limited to sealant additives, resins, etc., that repel water and prevent damage to the underlying substrate beneath the waterproofing material. In an embodiment, waterproofing agent may include but not limited to application of beeswax, waterproofing spray, or mink oil, lignin coating, ethylene propylene diene monomer EPDM rubber, hypalon, polyvinyl chloride, etc.

Embodiments of the disclosure are applicable to humans and more generally to mammals (host). Present disclosure provides a device for controlled delivery of drugs. "Drug" in context of the present disclosure may include any therapeutic active agent and/or a biologically active agent (i.e., an active ingredient in a pharmaceutical composition that is biologically active, such as a vaccine). The term drug as used herein is not limited by molecular weight of such agents. Terms "drug", "active agent", "therapeutic agent", "beneficial agent" or "pharmaceutical fluid" are used interchangeably. Drug as used herein refers to a single drug or multiple types of drugs. In some embodiments, the drug is one of injectable drugs such as, without limitation, Adalimumab, dulaglutide, enosumab, ustekinumab, pneumococcal 13-valent vaccine, romiplostim, paliperidone palmitate, erenumab, benralizumab, ixekizumab, ofatumumab, pegfilgrastim, guselkumab, golimumab, asfotase alfa, and blinatumomab. In some embodiments, the drug is a repurposed drug such as without limitation includes apixaban, lenalidomide, semaglutide, rivaroxaban, dapagliflozin, pomalidomide, fingolimod, ozanimod, tofacitinib, ambrisentan, axitinib, lenvatinib, and cariprazine.

An embodiment relates to a device comprising a permeability module comprising a semi-permeable membrane at one end of the device, an osmotic agent chamber comprising an osmotic solution (or osmotic agent), a sensor module comprising one or more sensors, a drug chamber comprising a drug, a piston, wherein the piston is sandwiched between the osmotic agent chamber and the drug chamber, a valve module to allow unidirectional flow of the drug from the drug chamber to outside the device through one or more drug outlet orifices present within the device, an electronic module, and a power supply module.

In an embodiment, an implantable drug delivery device has different modules such as without limitation, a permeability module, a sensor module, a drug module, a valve module, an electronics module, and a power module. These modules are interconnected with each other. A person skilled in the art would understand different ways of interconnecting these modules, such as but not limited to screwing them together, creating notches at the ends of the modules, etc. In some embodiments, each module is threaded with male-female threads such that the first module screws into the second module, the second module screws into the third module, and the third module screws into the fourth module.

In some embodiments, the sensor and permeability unit could be adhesively bonded to the device tube.

In an embodiment, on operation of the power supply module of the device: (i) the permeability module allows inflow of fluid from the semi-permeable membrane into the osmotic agent chamber to establish an osmotic pressure, (ii) the electronic module is configured to switch on and off the valve module as per a predetermined program set within the device to regulate flow of the drug from the drug chamber. In an embodiment, the inflow of a fluid through semi-permeable membrane into the osmotic agent chamber is on a real-time basis.

In an embodiment, the dose-to-dose variation of a drug via the device is ±25% or less by volume. In an embodiment, the dose-to-dose variation or flow discharge accuracy (used interchangeably throughout the specification) of a drug via the device is ±20% or less by volume. In an embodiment, the device has a dose accuracy of no wider than ±15% of the intended target dose.

In another embodiment, the flow discharge accuracy is ±10%. In another embodiment, the flow discharge accuracy is ±5%. In another embodiment, the flow discharge accuracy is ±3%.

Technical problem: Current drug delivery systems lack the capability to provide accurate and personalized medication dosages adapted to a patient's specific needs. These systems often rely on simple mechanical components, such as pistons regulated by osmotic pressure, without incorporating real-time measurement of piston displacement. This limitation results in potential over- or under-delivery of medication, leading to adverse effects, ineffective treatment, or complications in patient care. Furthermore, the inability to precisely control drug delivery exacerbates the challenges of managing complex conditions, particularly in patients with chronic illnesses, cognitive impairments, or in scenarios requiring strict drug administration, such as during the opioid crisis.

Technical solution: The active implantable medical device (AIMD) incorporates precise measurement and control of piston displacement to ensure accurate drug delivery. The device comprises a sensor module capable of real-time monitoring of the piston's longitudinal displacement, driven by osmotic pressure generated in an osmotic agent chamber. This displacement measurement is crucial, as it directly correlates to the volume of medication released from the drug chamber. The electronic module utilizes the sensor's data to communicate with a valve module, regulating the one-way flow of the drug with high precision. By continuously measuring and adjusting the piston's position, the system ensures consistent and accurate medication delivery, addressing the risks of over- or under-dosing and improving overall treatment efficacy.

Advantageous Effects: The active implantable medical device (AIMD) incorporates real-time measurement of piston displacement to ensure precise and consistent medication dosing, thereby reducing the risks of over- or under-dosing, enhancing treatment efficacy, and minimizing adverse effects, particularly in the management of chronic conditions or complex medication regimens. The integration of a sensor module and an electronic module allows for dynamic adjustments based on the displacement data, enabling personalized medication delivery tailored to individual patient needs. Additionally, the device's ability to regulate drug flow accurately through the valve module improves reliability, making it suitable for scenarios requiring stringent control, such as during opioid administration or in patients with cognitive impairments. The compact design of the AIMD further supports subcutaneous implantation, promoting patient comfort and adherence.

DESCRIPTION OF EMBODIMENTS

As an example, FIG. 1 illustrates an outside view of an active implantable medical device (AIMD) with a permeability module present at one end of said device according to one or more embodiments. The device is covered with a casing from outside. In an embodiment, the casing is made up of a biocompatible material or food and drug administration (FDA) approved material, such as without limitation, Titanium. In an embodiment, the casing has housing to connect different modules. As per the principle of the implantable, a person skilled in the art would understand different ways of putting electrical circuits in the casing, such as but not limited to gluing or imprinting. In some embodiments, the housing material provides durability, corrosion resistance, and compatibility with body, and fluids within the device, such as but not limited to titanium.

In an embodiment, the implantable device has a tubular structure. In an embodiment, the device tube has an outer diameter between 3 mm to 5 mm, such as 3 mm, 3.5 mm, 4 mm, 4.5 mm etc. In an embodiment, the casing has a wall thickness about 0.25 mm, 0.3 mm, 0.4 mm, 0.5 mm, 0.6 mm, 0.7 mm, 0.8 mm, 0.1 mm.

In an embodiment, the device as shown in FIG. 1 has a permeability module at one end to allow ingress flow of the fluid into the device. It has drug outlets to allow discharge of a drug present in the drug chamber to be released outside the device. In an embodiment, the drug outlet is present directly over or near the end of the drug chamber. In an embodiment, the drug outlets are present near the opposite end from the permeability module of the tube. In an embodiment, the drug outlet may be distributed over the area of the drug chamber.

Figure 2A:
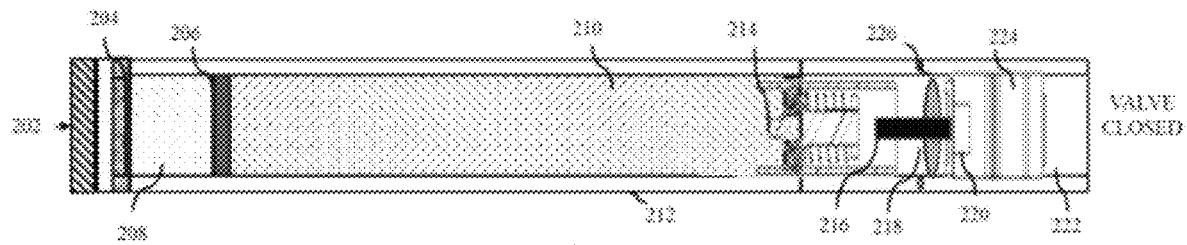
FIGS. 2A-2C illustrate inside views of an active implantable medical device (AIMD) in a valve open and closed state, according to one or more embodiments.
Figure 2B:
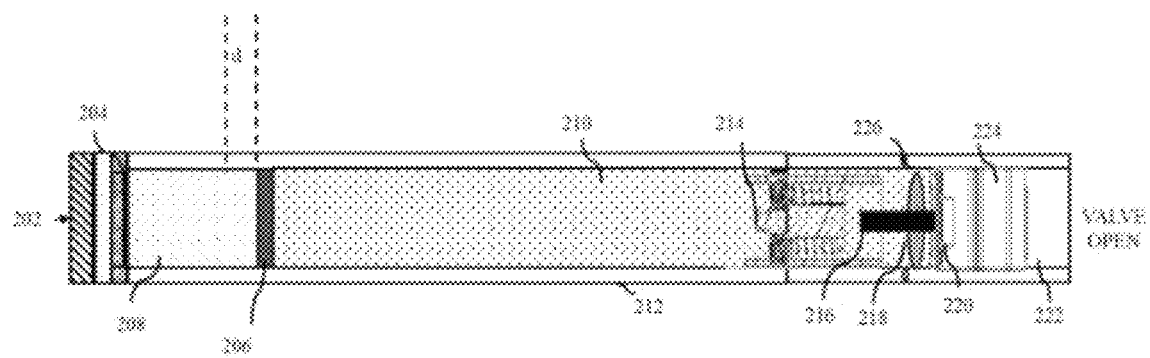
Figure 2C:
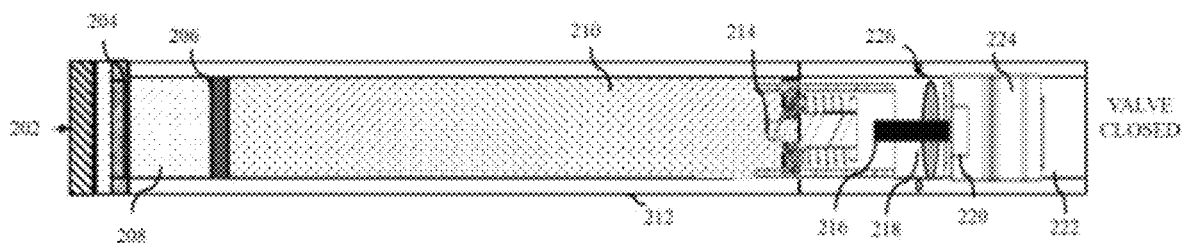

FIGS. 2A-2C illustrate inside views of an active implantable medical device (AIMD) in a valve open and closed state according to one or more embodiments. The active implantable medical device (AIMD) comprises a permeability module that comprises a semi-permeable membrane/plug 202, a sensor module that comprises a sensor 204, a piston 206, an osmotic agent chamber 208, a drug chamber 210, casing 212, and a drug outlet 226. The AIMD further comprises a valve module that comprises a relief valve 214, a push rod 216, a seal 218, and an actuator 220 and an electronic module that comprises electronics 224.

The permeability module allows ingress flow of a fluid to the osmotic agent chamber 208 and generates osmotic pressure. The piston 206 moves longitudinally within the AIMD in response to the osmotic pressure. The piston 206 may be a metallic piston or a non-metallic piston. The piston 206 may operate at a constant speed. For example, the piston 206 might move 0.1 mm every minute, and this rate of movement would remain the same throughout the operation of the device, ensuring a steady and predictable drug release rate.

The piston 206 may operate at a variable speed. For example, the piston 206 might start moving slowly, at 0.05 mm per minute, and then gradually accelerate to 0.2 mm per minute as the osmotic pressure increases. This allows the device to adjust the drug release rate based on real-time conditions and control over dosage delivery.

The drug chamber 210 comprises a drug and the valve module to allow one-way flow of the drug from the drug chamber 210 to outside the AIMD. The drug chamber 210 may comprise a threshold displacement limit. In an embodiment, the threshold displacement limit corresponds to a prescribed drug quantity, which may represent a maximum drug quantity intended to a subject. For example, in a 4 mm device, the threshold displacement limit could be set at 1 mm. When the piston 206 moves 1 mm, this displacement corresponds to the release of a specific amount of drug, such as 10 mg. The device is then programmed to stop further drug release once this 1 mm displacement is reached, ensuring that the prescribed dose is not exceeded. In another configuration of the 4 mm device, the threshold displacement limit might be set at 2 mm, where the movement of the piston 206 by 2 mm indicates that the maximum drug quantity (e.g., 50 mg) has been delivered. Once the piston 206 has moved 2 mm, no further displacement occurs, and the drug release is halted to prevent over-delivery.

In an embodiment, the subject is a living organism, which may be a mammal. In an embodiment, the mammal is a human being. The active implantable medical device (AIMD) is configured to be implanted subcutaneously in the subject. The active implantable medical device (AIMD) may be configured to utilize machine learning to adjust drug dosing according to a need of a user. To enable the use of machine learning for adjusting drug dosing according to the needs of the user, the AIMD incorporates an integrated system comprising sensors, algorithms, a drug delivery mechanism, and a feedback loop.

In an embodiment, the AIMD is equipped with sensors designed to continuously monitor the user's physiological parameters, such as blood glucose levels, heart rate, blood pressure, or other biomarkers that influence drug dosing. These real-time measurements are transmitted to an onboard processing unit, where the data is analyzed. The AIMD uses a machine learning module that processes this data to make dosing decisions. The machine learning algorithms may include supervised learning, pre-trained on datasets from multiple subjects, or reinforcement learning, which dynamically adjusts dosing based on trends and feedback specific to the individual user.

In an embodiment, the device creates a personalized drug-dosing model by analyzing historical data, physiological trends, and real-time feedback. This model adapts dynamically overtime, allowing for optimized dosing to suit the user's unique needs. The drug chamber 210 houses the medication and is equipped with the valve module that facilitates one-way flow of the drug from the chamber to the outside of the active implantable medical device (AIMD). The flow of the drug is controlled by the actuator 220, which operates based on dosages calculated by the machine learning algorithm.

To enhance safety, the AIMD incorporates fail-safe mechanisms and threshold limits. If the machine learning model produces dosing recommendations that fall outside of predefined safety parameters, the device may trigger an alert or revert to a default dosing regimen. The device also allows manual overrides by the user or a healthcare provider to address any unforeseen circumstances. In an embodiment, a continuous feedback loop is maintained within the AIMD, where the administered dosage and the user's physiological response are fed back into the machine learning model. This iterative process improves the model's accuracy and refines dosing predictions over time.

The active implantable medical device (AIMD) comprises a power module comprising a power source to power one or more components of the active implantable medical device (AIMD). The power source may be a battery 222.

In an embodiment, FIG. 2A shows position of valve state in the AIMD just after implantation in a host. The valve is closed, and the piston 206 is in a compressed state, that means the AIMD is activated. The active implantable medical device (AIMD) is activated to start operation either manually or automatically. On the activation of the electronic module, due to hypertonic solution present in the AIMD or more specifically permeability module, fluid (such as water) from the blood serum starts moving across the semi-permeable membrane into the hypertonic solution, entering the osmotic agent chamber 208 of the AIMD. In an embodiment, the hypertonic solution could be a solute such as NaCl or glucose.

Since the valves are closed, the ingress flow of fluid builds an osmotic pressure in the AIMD. When the valve (without limitation such as relief valve 214) opens, the piston 206 uncompresses thereby simultaneously releasing the drug outside. When the valve closes again, the osmotic pressure rises again compressing the piston 206. The active implantable medical device (AIMD) may be configured to discharge a fixed dose of the drug. The active implantable medical device (AIMD) may be configured to discharge a variable dose of the drug. In an embodiment, a dose-to-dose drug ejection variation from the active implantable medical device (AIMD) is less than ±25% by a predetermined volume. The dose-to-dose drug ejection variation may be ±10% or less by the predetermined volume.

When the relief valve 214 is closed and the AIMD is in equilibrium, the internal pressure in the osmotic agent chamber 208 and the drug chamber 210 will be the same. As the relief valve 214 opens and the drug starts delivering, the pressure in the drug chamber 210 decreases relative to the pressure in the osmotic agent chamber 208.

In an embodiment, in reference to FIG. 2B, when the valve is opened, the piston 206 displaces by a distance 'd' and therefore the shot size will be equal to the cross sectional area times d. Subsequently, when the valve is closed as shown in FIG. 2C, the piston 206 moves back a distance 'd'. In an embodiment, an amount of drug released in a single shot of the active implantable medical device (AIMD) equals the distance travelled by the piston times the cross sectional area of the active implantable medical device (AIMD). The sensor module measures a displacement of the piston 206 in real-time.

In an embodiment, the displacement of the piston 206 is proportional to an amount of discharge of drug. In an embodiment, the displacement of the piston 206 and the osmotic pressure within the permeability module has co-relation.

In an embodiment, the displacement is a linear displacement. The linear displacement refers to the piston 206 moving straight forward or backward along a fixed path (e.g., 1 mm in a straight line), without any lateral or curved motion. The movement is consistent and related to the distance covered along that line. In another embodiment, the displacement is a rectilinear displacement. The rectilinear displacement would mean that the piston 206 moves in a perfectly straight path (for example, 0.5 mm straight forward) from one point to another, ensuring no deviation in the direction of motion, such as sideways or angular movement. The motion remains confined to a straight line along the device.

The electronic module communicates a signal to the valve module to control the valve module and regulate the one-way flow of the drug based on the displacement of the piston 206. The electronic module may comprise a microcontroller. The valve module may comprise a flow switch. In an embodiment, the flow switch comprises an ON-OFF flow switch. The ON-OFF flow switch may comprise the relief valve 214, the push rod 216, and a stepper motor.

In some designs of the implantable device the spaces of the piston 206 are filled with gas. In an embodiment, the energy required to compress the spring is derived from the Gibbs potential across a permeability membrane, utilizing the body's osmotic pressure. In an embodiment, the device utilizes Gibbs free energy to drive the piston 206. In an embodiment, a time taken for fluid to flow through the semi-permeable membrane 202 will be several orders of magnitude higher than the time it takes for the drug to be ejected out via the displaced piston. When the relief valve 214 opens, the pressure drops, that means, theoretically some fluid is going to start increasing, but between the opening and closing of the valve, the amount of the fluid that will ingress flow through the permeable membrane will be almost negligible compared to the volume of fluid that has been discharged via drug outlets.

In an embodiment, the piston 206 is like a spring, therefore the time to move a distance 'd', will be almost instantaneous, whereas the time for that amount of volume of fluid to ingress flow through the semi-permeable membrane will possibly be in several hours, minutes to hours.

In an embodiment, the opening and closing of the valve occurs repeatedly in a cycle, allowing the piston 206 to compress and uncompress alternately.

In an embodiment, a rate of osmotic exchange needs to be assessed to determine the rate of pressure change in the osmotic agent chamber 208 during drug delivery based on the permeability of the semi-permeable membrane 202 since this could also affect distance "d" travelled by the piston 206. If the rate of osmotic exchange is very low, the pressure in the osmotic agent chamber 208 will likely remain the same as the pressure in the equilibrium condition.

In an embodiment, a rate of osmotic exchange needs to be assessed to determine the rate of pressure change in the osmotic agent chamber 208 during drug delivery based on the permeability and conductance of the semi-permeable membrane.

Figure 3A:
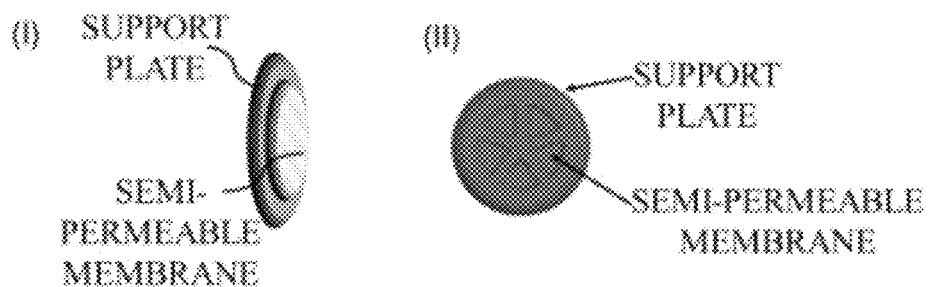
FIG. 3A illustrates a schematic of a flat membrane as a permeability module, according to one or more embodiments.

FIG. 3A illustrates a schematic of a flat membrane as a permeability module according to one or more embodiments. The permeability module functions to seal the interior of the AIMD from the external environment, allowing only specific molecules to permeate through a membrane plug into the device's interior. In an embodiment, the permeability module also effectively prevents items within the AIMD, such as an osmotic agent and a drug from passing through it. In an embodiment, the first end of the permeability module has the semi-permeable membrane (or membrane plug) supported by a plate, and the other end of the permeability module has holes to allow fluid inflow inside the device. In an embodiment, the permeability module may have a hollow fiber or bundles of hollow fibers arranged together, forming a bridge for entry of outside fluid into the device. In an embodiment, the permeability module may also be designed to separate solutes from a feed solution, such as blood serum, using a semi-permeable membrane.

In an embodiment, the permeability module has a permeability membrane held by a support structure as shown in FIG. 3A. In an embodiment, the support structure or plate or disc could be made of a biocompatible material and/or metal such as without limitation titanium, FDA approved material such as stainless steel. In some embodiments, the semi-permeable membrane is supported by one plate or sandwiched between two plates. These plates have a plurality of holes. The arrangement of the plate holes determines the flow rate of fluid passing through them. (Liquid or fluid are interchangeably used throughout the description.)

In an embodiment, the ingress flow of the fluid can be adjusted by adjusting the alignment of the discs/plates. When the discs/plates are aligned differently, the flow rate changes. When the rigid discs are aligned such that none of the holes from the first plate overlay the holes in the second plate, the flow rate through the sandwich structure is nearly zero. Conversely, when the rigid discs are aligned such that all the holes in the first plate overlay the holes in the second plate, the flow rate through the sandwich structure is maximum. By aligning the rigid discs so that partial areas of the holes in the first plate overlay the holes in the second plate, the flow rate is between nearly zero and the maximum. This intermediate configuration allows fine-tuning of the ingress rate. In some embodiments, ingress flow rate of fluids through the permeability module could be adjusted by changing the membrane's permeability or its thickness.

In an embodiment, the discs/plates are made of rigid material. In some embodiments, the discs/plates are made of flexible material.

Figure 3B:
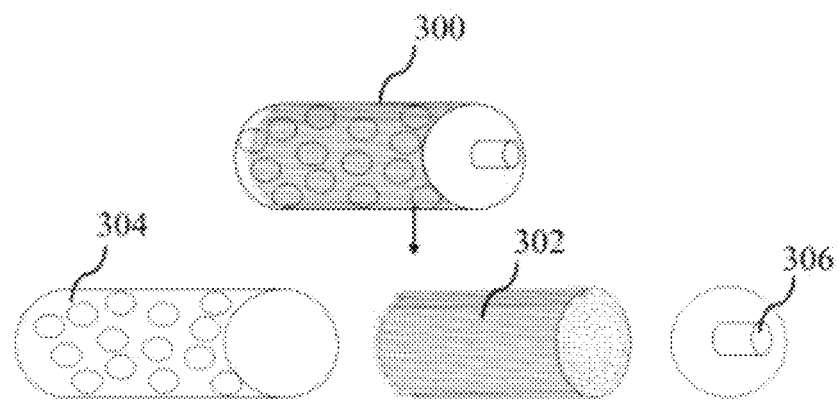
FIG. 3B illustrates a schematic of hollow fiber membrane as a permeability module, according to one or more embodiments.

In an embodiment, a permeability module may contain a hollow fiber membrane. As shown in FIG. 3B, a hollow fiber membrane 300 comprises numerous thin, flexible fibers 302 bundled together in a casing 304. Each fiber has a hollow core, allowing fluid to flow through. Both ends of the fibers, on the right side and the left side of the casing are U shaped.

In one embodiment, the hollow fiber membrane is a forward osmosis membrane and comprises an inlet end facing the first end of the device and an outlet facing towards a sensor module. These membranes utilize the natural osmosis process, where fluid moves from a low concentration to a high concentration through the membrane. Natural osmosis requires lower energy compared to traditional reverse osmosis systems that operate under lower pressure conditions within hollow fibers.

In an embodiment, one or more hollow fibers are made up of semi-permeable membrane. In an embodiment, the hollow fibers comprise a solute solution such as but not limited to glucose solution (G) as shown in FIG. 3B. The high concentration of the glucose solution allows natural osmosis to happen within the device. As fluid ingresses from the body into the permeability module, an almost equal volume of the glucose solution will be pushed out from the permeability module through the opening at the second end 306 of the module. The hollow fiber forward osmosis membranes are thin and flexible. In some embodiments, the hollow fibers contain solutes such as but not limited to NaCl.

Figure 4:
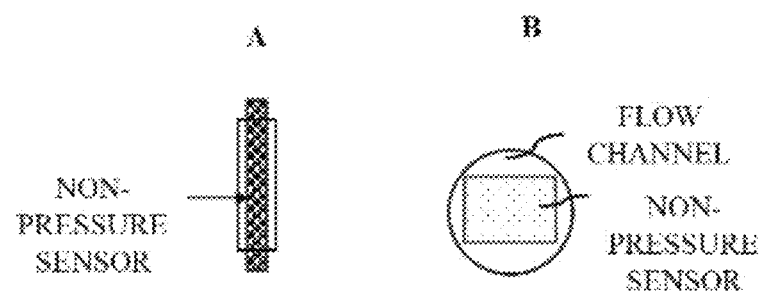
FIG. 4 illustrates a schematic of the front view of the sensor module and the cross sectional view of the sensor module taken from the permeability side of the AIMD, according to one or more embodiments.

In an embodiment, the implantable device has a sensor module. An example of a sensor module is shown in FIG. 4. The sensor module measures the displacement of the piston in real-time. The sensor module comprises one or more non-pressure-based sensors, including but not limited to Linear Variable Differential Transformers (LVDTs), magnetic position sensors, optical sensors, ultrasonic sensors, capacitive displacement sensors, inductive displacement sensors, capacitive proximity sensors, inductive proximity sensors, inductive impedance sensors, capacitive impedance sensors, eddy current-based impedance sensors, and resonance-based impedance sensors. The displacement may be a linear displacement. The displacement may be a rectilinear displacement. In an embodiment, the sensor module measures the displacement of the piston through a non-contact measurement. In an embodiment, the sensor module measures the displacement of the piston through a contact measurement.

A person skilled in art would recognize various modes of attaching these sensors within the principle of operation of the device. In an embodiment, sensors may be embedded and/or attached to a definite structure of the device, such as a ring-like structure.

In an embodiment, the magnetic position sensors, functioning based on magnetic sensing, comprise a small biocompatible magnet, such as a neodymium magnet, which can be easily integrated inside the tube and attached to the piston. External magnetic position sensors, such as Hall effect sensors or magnetometers, detect changes in the magnetic field generated by the magnet as the piston moves. These variations provide a reliable, non-contact measurement of the displacement, ensuring durability and long-term functionality.

In an embodiment, the optical sensors, functioning based on fiber optic sensing, comprise fiber optic cables with diameters as small as 200-400 μm that can be embedded alongside the piston or integrated into the tube wall. Using advanced optical mechanisms such as Fabry-Perot interferometers or Fiber Bragg Gratings (FBG), these optical sensors measure displacement with exceptional precision by analyzing light interference or wavelength shifts.

In an embodiment, the capacitive displacement sensors or inductive displacement sensors, functioning based on capacitive and inductive sensing techniques, further enhance the versatility of the sensor module. In an embodiment, the capacitive displacement sensors or inductive displacement sensors comprise miniaturized electrodes, such as thin-film electrodes, or wire-wound coils that can be integrated into the tube or piston surface. In an embodiment, the capacitive displacement sensors function by detecting changes in capacitance caused by the piston's movement, while inductive displacement sensors monitor variations in inductance or magnetic coupling.

In an embodiment, the capacitive or inductive impedance sensors, functioning based on impedance-based sensing, comprise electrodes for impedance sensing that can be printed or embedded directly onto the tube wall or piston surface. Displacement is measured by monitoring changes in impedance, which vary based on the relative position of the piston.

The sensor module transmits real-time displacement data to the electronic module, which processes this information to regulate the valve module and ensure drug delivery.

In some embodiments, a sensor is designed to fit snugly inside a cylindrical space with specific dimensions (for example within 5 mm×4 mm). This compact design allows for easy integration into various applications. In some embodiments, a sensor's housing material is titanium, which provides durability, corrosion resistance, and compatibility with the fluid.

Figure 5:
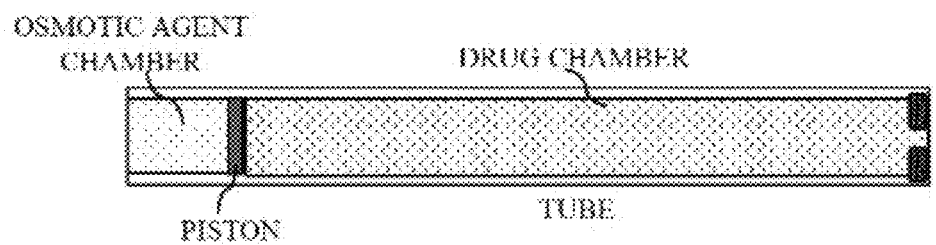
FIG. 5 illustrates a schematic of a drug module, according to one or more embodiments.

In an embodiment, the implantable device has a drug module. An example of a drug module is shown in FIG. 5. Referring to FIG. 5, a drug module includes a drug chamber. The drug chamber contains drug Df. In an embodiment, the drug chamber has a diameter between 3 mm to 5 mm, such as 3 mm, 3.5 mm, 4 mm, 4.5 mm, etc. The drug chamber is separated by an osmotic chamber and a piston. The drug Df without limitation could be any known drug or its conjugated form, or chelated form, etc., or within a vehicle such as beads, or in forms such as without limitation microparticles, liquid, etc., understood by a person skilled in the art within contemplated disclosure.

The piston is configured to eject a drug volume within a substantially short period of time compared to the time it takes a volume of one dose of fluid flowing through the permeability membrane (i.e., ejecting a dose in a few seconds.) This way, the power required to open and shut the relief valve is extremely low.

In some embodiments, a piston movement utilizes energy from an energy source present in the power module of the device.

In some embodiments, a sensor measures and determines the position of the piston. The position of the piston is used to determine if the implantable device is functioning correctly. In case, the prediction for the piston displacement is incorrect, then the implantable device will send a signal to the patient and/or a caregiver about a possible defect in the implantable device and the device must be immediately removed. The drug in the drug chamber is pushed due to osmotic pressure exerted by the osmotic agent in the osmotic agent chamber via the piston. The piston is operable to move a distance 'd' to deliver a constant volume of the drug Df for each shot via an On-Off flow switch. The final osmotic agent concentration ($C_f$) required to facilitate the release of the last dose of the drug from the device will dictate the amount of osmotic agent (M) added in the osmotic pump chamber.

The maximum operating pressures of the ON/OFF flow switch will dictate the maximum allowable osmotic pressure ($\pi_{max}$) in the osmotic pump chamber. The maximum allowable osmotic pressure ($\pi_{max}$) will determine the initial osmotic agent concentration ($C_i$) in the osmotic pump chamber. The initial osmotic agent concentration ($C_i$) in the osmotic pump chamber and the amount of osmotic agent (M) added in the osmotic pump chamber will determine the initial volume ($V_i$) of the osmotic pump chamber. The maximum ingress rate will occur at the start of operation of the implantable device. The maximum flow rate of the drug formulation will be based on the volume discharged per dose. Assume that the volume discharged per dose per week is 10 µl. A membrane may be chosen having a permeability such that ingress flow will take about 10 minutes under the maximum ingress rate and the initial osmotic agent concentration ($C_i$). If the time of drug discharge is at least 10 minutes per dose, the ON/OFF flow switch can be switched without substantial fluctuations in the drug formulation discharge.

The osmotic pressure $\pi$ in the osmotic pump is iCRT, where $\pi$ is the osmotic pressure and i is the Van't Hoff factor, and c is the concentration of osmotic agent. Assume $L_1$ is the initial and $L_2$ the final position of the piston before and after displacement of the piston under osmotic pressure. The piston displacement D as a function of osmotic pressure $\pi$ is calculated as:

$$D = \frac{2CRT}{A}\left(\frac{1}{\pi 2} - \frac{1}{\pi 1}\right) \quad \text{Equation (I)}$$

where R is ideal gas constant, T is temperature, C is concentration of osmotic agent, A is cross sectional area, $\pi 1$ is initial osmotic pressure and $\pi_2$ is current osmotic pressure.

As per Equation (I), the displacement of the piston is correlated to the osmotic pressure ($\pi$) in the osmotic chamber. To start a dose, the osmotic pressure ($\pi_1$) is recorded, and the on-off switch is turned on. Then, when the osmotic pressure drops to ($\pi_2$), which according to Equation (I) denotes a piston movement of d, the on-off flow switch is turned off. In this manner, the implantable device discharges a precise dose from the drug chamber to the exterior of the implantable device. This drug discharge process is repeated for each dose.

In an embodiment, the implantable device controls drug discharge according to equation (1). Monitor the pressure ($\pi_1$) and L1 as soon the valve opens. Allow the valve to remain open, till the pressure drops to $\pi_2$. Now the piston has moved to distance L2. Discharge of drug flow from the device is (L2-L1)*cross sectional area of the piston.

In an embodiment, the piston position does not control the opening and closing of the relief valve. By the above approach, dosing and checking for proper functioning of the implantable device is decoupled. In an embodiment, the piston position controls the opening and closing of the relief valve.

Figure 6A:
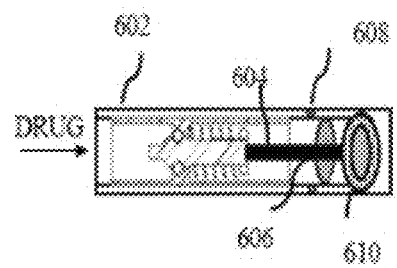
FIG. 6A illustrates a schematic of an internal view of an on-off flow switch/valve module, according to one or more embodiments.

In an embodiment, the implantable device has a valve module. An example of a valve module is shown in FIG. 6A. In an embodiment, the implantable device may have a valve that may be an active valve configured to be electronically controlled. In an embodiment, the device may have more than one valve. In an embodiment, the second valve may be a passive one-way valve. The electronically powered pump may be a first electronically powered pump, and the pump assembly may include a second electronically powered pump, where the first valve is disposed in series with the first electronically powered pump, the second valve is disposed in series with the second electronically powered pump, and the second electronically powered pump is disposed in parallel with the first electronically powered pump. In some examples, the first electronically powered pump is activated and the second electronically powered pump is deactivated in response to the implantable device being in the compressed mode, and the first electronically powered pump is deactivated and the second electronically powered pump is activated in response to the implantable device being in the deflation mode.

In an embodiment, a valve may include a passive one-way valve. In some examples, the passive one-way valve includes a duckbill valve. In some examples, the passive one-way valve includes a movable valve component (e.g., ball, poppet, etc.) and a biasing member (e.g., a spring). The electronic module configures and controls the valve module such that the valve module is switchable between open and close states in response to commands provided by the electronic module.

Referring to FIG. 6A, the valve module is enclosed within a casing 602, acts as an ON-OFF flow switch and comprises a spring loaded relief valve (like a bicycle tube valve) with a ball and a seat coupled to an actuator 610 (e.g. stepper motor with helical shaft or vibratory motor, etc.) with a push rod 604, to push the head of the relief valve opening the seal 606, thereby creating a slight gap between the ball and the seat of the relief valve. The actuator is powered via the electronics module and power module. The drug is released from drug outlet 608.

Figure 6B:
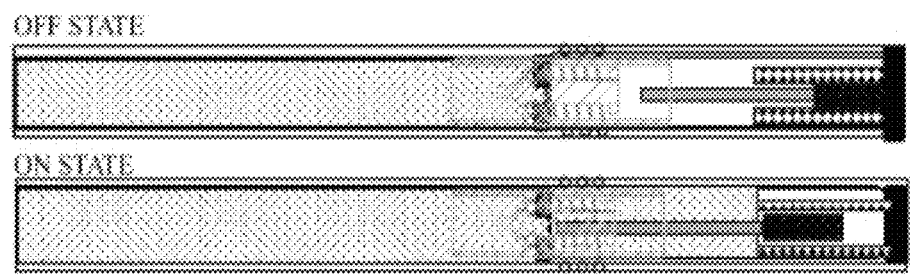
FIG. 6B illustrates the ON and OFF state of the valve module, according to one or more embodiments.

In an embodiment, FIG. 6B shows the position of the valve module in the OFF state and the ON state.

Figure 6C:
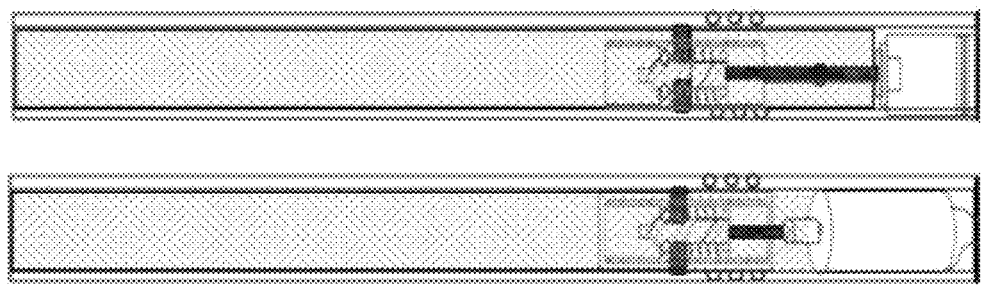
FIG. 6C illustrates the operation of (i) stepper motor, (ii) and vibratory motor as an actuator for actuating a push rod to open a valve such as a relief valve, according to one or more embodiments.

In an embodiment, the device has a stepper motor. FIG. 6C shows the use of a stepper motor and a vibratory motor as actuators for actuating a push rod for opening and closing of the relief valve.

In an embodiment, a stepper motor may work in the following way: connected to a screw via a coupler, responsible for initiating movement. When the stepper motor rotates, it turns the screw, driving a nut threaded onto it. This rotation causes the nut to move linearly along the screw, with the direction of movement determined by the motor's rotation. The nut will attach to a push rod, and as the nut moves, it will push or pull the rod, creating linear motion. This motion will be directly linked to the relief valve opening or closing by applying force to the valve's mechanism. Control of this process could be managed by a stepper motor driver, which will receive signals to control the motor's speed, direction, and movement distance.

In an embodiment, a processor could send signals to the motor drivers, dictating the motor's operation and, consequently, the position of the push rod and relief valve. For example, when the processor sends a signal to rotate the motor in a specific direction, the nut and push rod will move, opening the relief valve. Conversely, when the motor's direction is reversed, the nut and push rod will retract, closing the valve. This system will allow for highly accurate regulation of the valve's opening and closing providing precise control over the flow or pressure of the fluid in the system.

A vibratory motor, instead of providing rotational motion, generates oscillating vibrations. A vibratory motor would be connected to the screw or another mechanism capable of converting the vibrations into linear motion. In the setup of FIG. 6C, the vibratory motor will generate oscillating motion, which is transferred to a push rod via a mechanical linkage, such as an eccentric cam or lever. The vibratory motion causes the push rod connected to a relief valve to move back and forth, thereby opening and closing the valve.

Figure 6D:
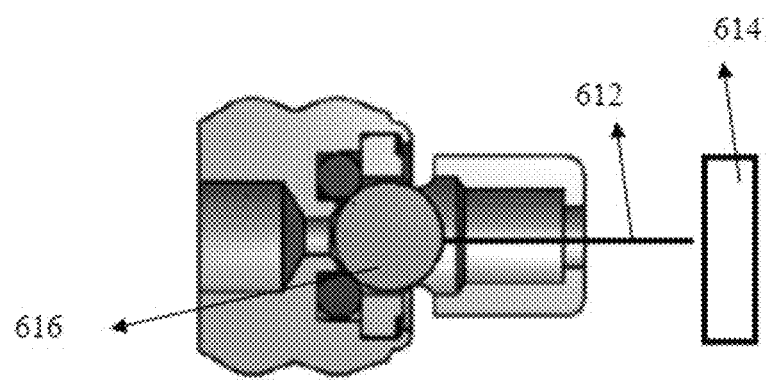
FIG. 6D illustrates a valve without a stepper motor, according to one or more embodiments.

FIG. 6D illustrates a valve without a stepper motor, according to one or more embodiments. In this embodiment, the valve module is free of motor (e.g., stepper motor). As shown in FIG. 6D, the valve has a vibrating plate 614 with a plunger needle-like structure 612 adapted to fit in a 4 mm device. The needle-like structure 612 is made up of a biocompatible material. The needle-like structure 612 is not in contact with the vibrating plate 614 when the valve is in OFF state. The valve functions as a relief valve (e.g., spring loaded relief valve). When the vibrating plate 614 is powered by a power module, it vibrates and the plunger needle-like structure 612, meets the vibrating plate 614, pushing the relief valve (like a push rod pushing the head of the relief valve) to open (ON). At the opposite side of the plunger, the plunger needle-like structure 612 is connected to a ball or a ball-like structure 616. The needle-like structure 612 may comprise an internal diameter of 100-200 μm. The plunger needle-like structure 612 pushes the head of the relief valve from a direction which is opposite to the one-way flow of the drug.

The ball-like structure 616, acts as a physical barrier to control the drug's movement. The ball-like structure 616 allows drug flow only when a force from the direction opposite to the one-way flow of the drug, such as pressure generated by the vibrating plate 614, displaces the ball-like structure 616 momentarily, enabling a precise amount of the drug to enter the needle. Upon actuation, the vibrating plate 614, connects to the plunger needle-like structure 612, generating controlled oscillatory motions (vibrations), which are transmitted to the needle-like structure 612.

The vibrations are carefully calibrated in terms of frequency and amplitude to match the fluid properties of the drug (e.g., viscosity) to ensure smooth, consistent delivery, controlled flow rate and to prevent blockage. The flow rate may be 1-10 μL/hour. The vibrating plate 614 may oscillate at a frequency range of 20-50 kHz. These vibrations serve two purposes: they facilitate the smooth flow of the drug through the needle by reducing resistance and preventing clogging, ensuring consistent delivery. The needle-like structure 612 attached to the vibrating plate 614 acts as the final conduit for the drug's release into the target tissue. The vibrations may also improve the dispersion of the drug into the surrounding tissue after it exits the needle-like structure 612.

Different power sources could be employed by valves for its operations. Some examples of power sources that could be employed by a valve module are explained in the below embodiments of this disclosure.

An implantable device of the present disclosure has a power supply module along with other modules, parts, and features. The electronic module and/or the power supply module is/are separated from the rest of the modules of the device by a waterproofing (or another fluid tight barrier). A power module of an implantable drug delivery device comprises at least one power source and a power switch. In some embodiments, the power source is a rechargeable power storage, harnessing energy from the environment, for example: energy could be harvested by converting kinetic energy of body movements into electrical power, or by utilizing body heat to generate power, or by capturing energy from the heartbeat, or by using the body's electromagnetic fields. In some embodiments, the device receives power through induction charging from an external source. In some embodiments, the power switch is a magnetic field activated switch. The power switch can also utilize other mechanisms available in the environment to turn the power on permanently. The power source and the power switch work together to ensure the device operates reliably, utilizing available energy efficiently and maintaining a consistent power supply. The device relies on a wireless charger to recharge its rechargeable battery, ensuring a continuous supply of electric power.

In some cases, the power source is a coin battery or button battery. A coin battery is a small battery made of a single electrochemical cell and shaped as a squat cylinder typically 5 to 25 mm (0.197 to 0.984 in) in diameter and 1 to 6 mm (0.039 to 0.236 in) in height, resembling a button. A coin battery is adapted to achieve a reduced size AIMD. Stainless steel usually forms the bottom body and positive terminal of the cell; insulated from it, the metallic top cap forms the negative terminal. Batteries employed in the power module could be either primary cells or rechargeable secondary cells. It is also possible that the device has a combination of primary and rechargeable secondary cells.

The power from the power source module is distributed to one or more components of the device such as sensors, piston, valves, etc. Distribution of power to various components of the device is controlled by the electronic module. For example: a processor or simple timer of the electronic module manages the device's operations, including recording and adjusting medication dosing based on sensor inputs, monitoring fault conditions, processing sensor data for accurate operation, and overseeing battery status and power usage. In an embodiment, the processor may also store relevant patient medical history for reference. The system ensures that the implantable drug delivery device operates efficiently and effectively, providing necessary treatment while maintaining patient safety.

Figure 6E:
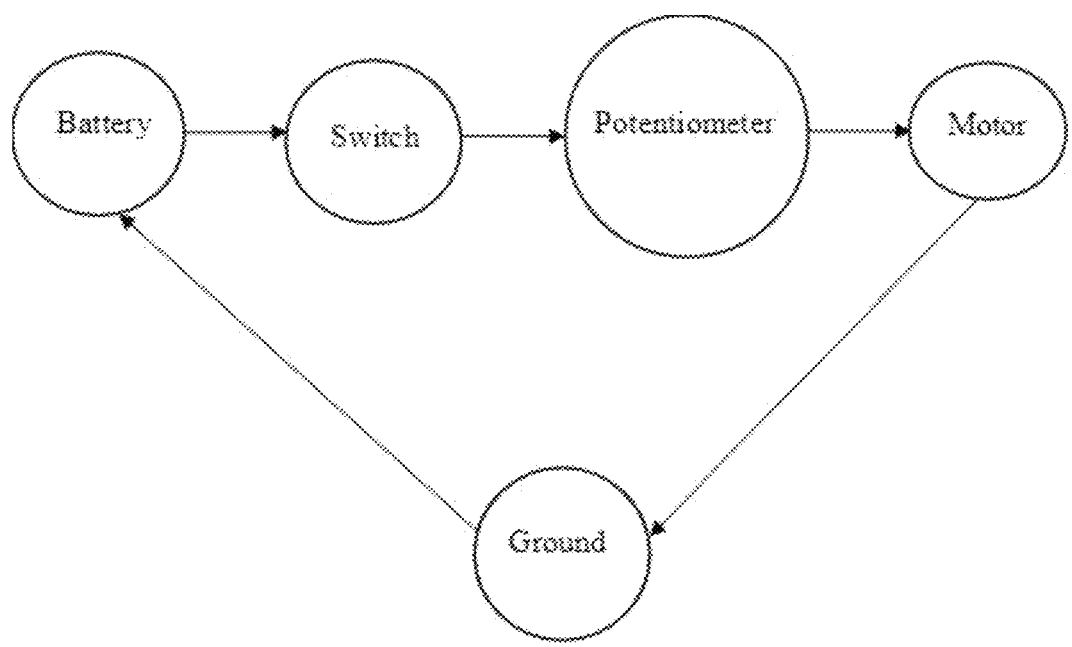
FIG. 6E illustrates a wiring diagram of a vibrating plate circuit, according to one or more embodiments.

FIG. 6E illustrates a wiring diagram of a vibrating plate circuit, according to one or more embodiments. The vibrating plate circuit comprises a battery, a switch, a potentiometer, a motor and a ground. All of the above mentioned components are in the size range of less than 5 mm. The battery is adapted to provide power to the circuit. The battery may be a button cell battery. The switch controls the ON/OFF state of the motor (e.g., Precision Microdrive 310-103, Precision Microdrive 304-116). The motor may be a coin vibration motor (cylindrical or pancake-shaped). The potentiometer is adapted to adjust the motor's speed. Adjusting the motor speed adjusts the vibration intensity. The motor comprises an eccentric weight attached to the motor. The eccentric weight is a small piece of metal or plastic that can be attached to the motor shaft off-center. The eccentric weight is fixed to the motor such that it has enough room to rotate without hitting the plate or other parts. The eccentric weight is adapted to create vibrations when the motor spins. The eccentric weight is securely attached and balanced to the motor to avoid excessive wear on the motor.

The motor may be attached to the vibrating plate using several methods. Some of them are 1) Direct Adhesive Attachment, 2) Clamping, 3) Screw mounting, 4) 3D-Printed Motor Holder, 5) Elastic Bands, 6) Foam or Rubber Dampers. The motor may be attached to the vibrating plate using strong adhesives like epoxy glue, hot glue, or double-sided industrial-grade adhesive tape to secure the motor to the underside of the plate. The adhesives are vibration resistant. The motor may be clamped to the vibrating plate using small brackets or clamps. This is useful for removable designs where you might need to replace the motor. If the motor has mounting holes, the screws or bolts may be used to attach it to the plate. Corresponding holes may be drilled in the plate for precise alignment. A custom motor mount may be 3d-printed to hold the motor snug and can be glued or screwed to the plate. In an embodiment, rubber bands or elastic straps are used to tightly hold the motor against the plate. In another embodiment, the motor may be placed on a thin foam pad or rubber strip before attaching it to the plate to reduce noise and stress on the motor.

Figure 6F:
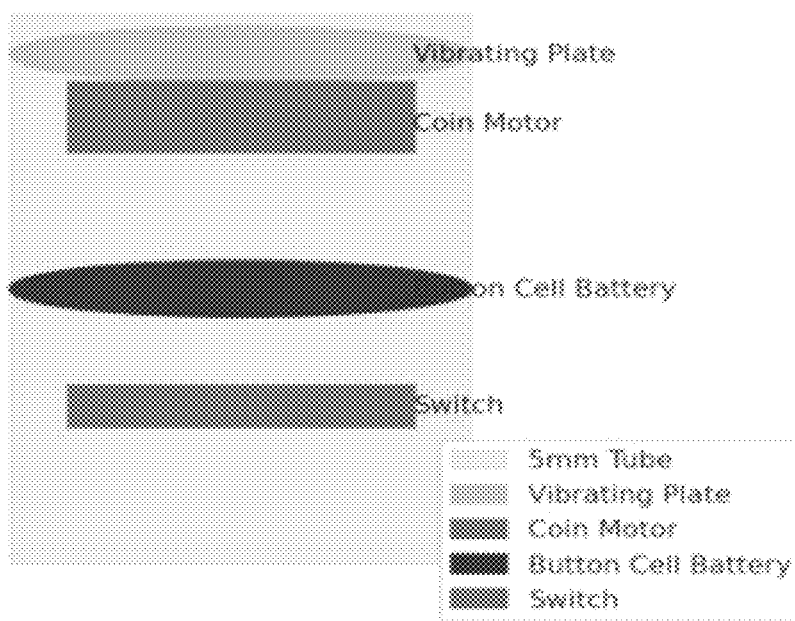
FIG. 6F illustrates an arrangement of components of a vibrating plate for a 5 mm device, according to one or more embodiments

FIG. 6F illustrates an arrangement of components of a vibrating plate for a 5 mm device, according to one or more embodiments. The vibrating plate is attached directly to the motor shaft (not shown in FIG.) to achieve compact sized AIMD. The motor adapted to actuate the vibrating plate may be a coin motor. The coin motor is compact and fits snugly within the tube of the AIMD (5 mm). A button cell battery may be positioned below the motor to power the system. The switch may be a miniature tactile, or reed switch located at the base.

The reed switch may be a magnetic sensing component. The reed switch enables the device to respond to external magnetic fields for activation, deactivation, or control of the vibrating plate mechanism. The reed switch is a small, biocompatible, sealed device consisting of two thin ferromagnetic metal reeds inside a glass tube. When exposed to a magnetic field, the reeds come into contact (or separate, depending on the design), completing, or breaking an electrical circuit. The reed switch acts as an on/off switch for the device. By bringing a magnet near the implant, the switch closes or opens the circuit, activating or deactivating the vibrating plate. The reed switch allows external control of the device using a magnet. The reed switch can be part of a feedback loop where the external magnet also triggers monitoring or diagnostic functions.

Figure 7A:
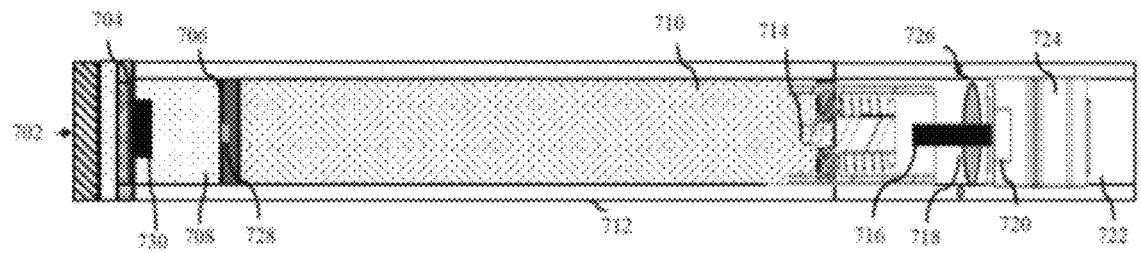
FIG. 7A is a schematic diagram illustrating a magnetic sensing mechanism for measuring the displacement of a piston in the active implantable medical device (AIMD), according to one or more embodiments.

FIG. 7A is a schematic diagram illustrating a magnetic sensing mechanism for measuring the displacement of a piston in the active implantable medical device (AIMD), according to one or more embodiments. The active implantable medical device (AIMD) comprises a semi-permeable membrane/plug 702, a sensor 704, a piston 706, an osmotic agent chamber 708, a drug chamber 710, casing 712, a relief valve 714, a push rod 716, a seal 718, an actuator 720, a battery 722, electronics 724, and a drug outlet 726. The function of these components has been explained above.

In an embodiment, the magnetic sensing mechanism operates using a magnetic position sensor. As shown in FIG. 7A, the magnetic position sensor comprises a small biocompatible magnet 728, which is attached to the piston 706. The magnet moves along with the piston inside the tube. In an embodiment, the AIMD comprises an external magnetic sensor 730 positioned inside the tube, designed to detect changes in the magnetic field as the magnet moves with the piston 706. In an embodiment, the AIMD comprises the external magnetic sensor 730 positioned outside the tube. In an embodiment, the external magnetic sensor 730 is positioned in close proximity to the magnet 728 to accurately detect and analyze the magnetic field changes.

The magnet 728 is designed to generate a magnetic field, and as it moves with the piston 706, it causes variations in the strength and orientation of the magnetic field. This change in the magnetic field is detected by the external magnetic sensor 730, which can be, for example, a Hall effect sensor or a magnetometer. In an embodiment, the external magnetic sensor 730 measures the fluctuations in the magnetic field generated by the magnet as it moves. These variations in the magnetic field correspond to the displacement of the piston 706, allowing the external magnetic sensor 730 to track the piston's position. By analyzing the changes in the magnetic field strength and direction, the external magnetic sensor 730 can determine the position of the piston 706 in real-time.

Figure 7B:
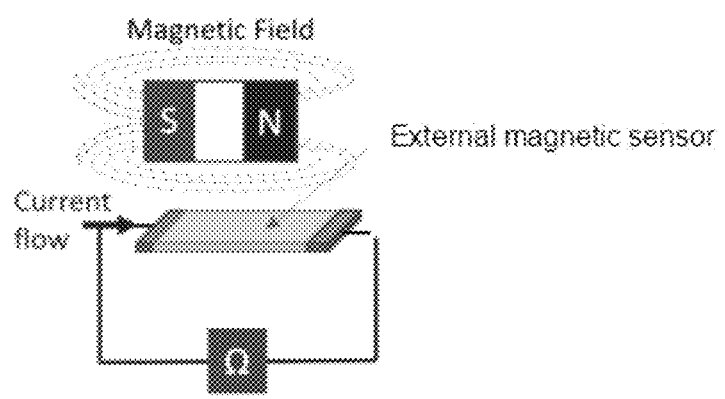
FIG. 7B illustrates the working principle of an external magnetic sensor, according to one or more embodiments.

FIG. 7B illustrates the working principle of an external magnetic sensor 730 according to one or more embodiments. The diagram shows a magnet with defined North (N) and South (S) poles, creating a magnetic field around it. The external magnetic sensor 730 is positioned in such a way that it can detect this magnetic field.

The external magnetic sensor 730 measures the changes in the magnetic field as the magnet moves. As the magnet's field interacts with the sensor, it induces a current flow within the sensor's circuitry. The diagram also shows the flow of current through the sensor, which is correlated with the strength and direction of the magnetic field. The resistance (Q) in the circuit can be used to quantify the changes in the magnetic field. The changes in the magnetic field strength and direction correspond to the displacement of the piston.

Figure 7C:
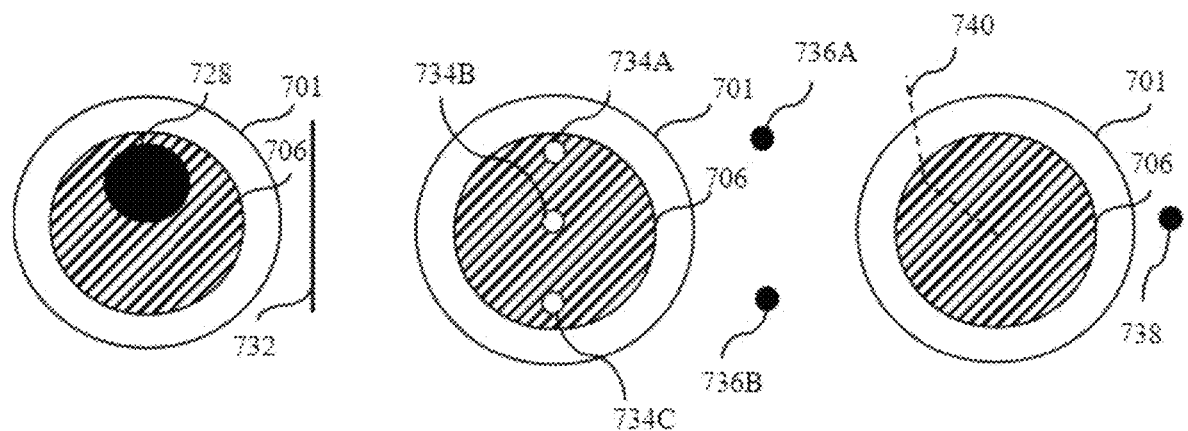
FIG. 7C illustrates three different configurations of magnetic sensing mechanism within a 4 mm diameter tube, according to one or more embodiments.

FIG. 7C illustrates three different configurations of magnetic sensing mechanisms within a 4 mm diameter tube according to one or more embodiments. In an embodiment, the active implantable medical device (AIMD) has a tubular structure. The tube is designed with an outer diameter of 4 mm, as illustrated in FIG. 7C and labelled as the 4 mm diameter tube 701. In an embodiment, the left side figure of FIG. 7C illustrates the small biocompatible magnet 728 attached directly to the piston 706 inside the active implantable medical device (AIMD). As the piston 706 moves, the small biocompatible magnet 728 moves with it. An external magnetic sensor 732 placed outside the tube detects the magnetic field generated by the magnet. This allows for the precise measurement of the piston's position based on the strength and direction of the magnetic field detected by the sensor. This method is simple and effective for tracking linear displacement in applications where space constraints are a concern.

In an embodiment, the middle figure of FIG. 7C illustrates one or more small magnets 734A, 734B, and 734C distributed along the inner or outer surface of the tube. A set of external magnetic sensors 736A and 736B detects the piston's position by measuring the changes in the magnetic field strength or orientation as the piston moves. This arrangement improves displacement tracking across a broader range, making it ideal for systems that demand precise measurements.

In an embodiment, the right side figure of FIG. 7C illustrates a magnet with a gradient field 740 that is integrated into the piston. The gradient field 740 (illustrated as dotted line) changes as the piston moves, and a gradient field sensor 738 detects these changes to determine the piston's position. This method is ideal for systems that require continuous and precise tracking of the piston's movement. The dotted line representing the magnet's gradient field provides data on the piston's displacement, facilitating precise monitoring across its entire range of motion.

Figure 8A:
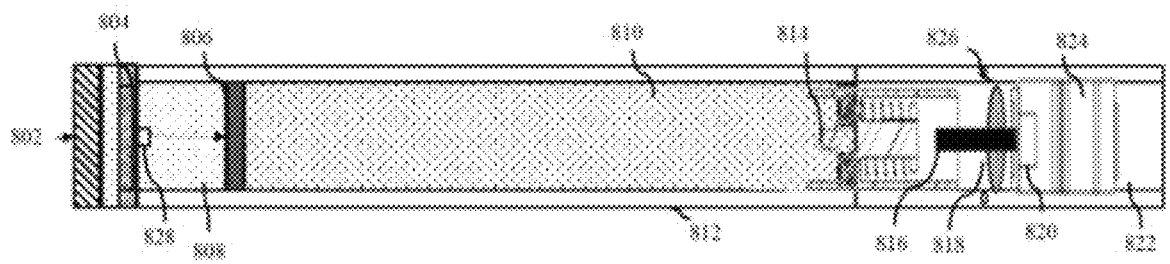
FIG. 8A is a schematic diagram illustrating a fiber optic sensing mechanism for measuring the displacement of a piston in the active implantable medical device (AIMD), according to one or more embodiments.

FIG. 8A is a schematic diagram illustrating a fiber optic sensing mechanism for measuring the displacement of a piston in the active implantable medical device (AIMD) according to one or more embodiments. The active implantable medical device (AIMD) comprises a semi-permeable membrane/plug 802, a sensor 804, a piston 806, an osmotic agent chamber 808, a drug chamber 810, casing 812, a relief valve 814, a push rod 816, a seal 818, an actuator 820, a battery 822, electronics 824, and a drug outlet 826. The function of these components has been explained above.

In an embodiment, the fiber optic sensing mechanism operates using a fiber optical sensor 828. The fiber optical sensor 828 relies on micro-diameter optical fibers, typically ranging from 200 to 400 µm in diameter, which can be integrated alongside the inner wall of the tube or directly within the piston 806. The fiber optical sensor 828 emits light and detects reflected or scattered light, to measure the displacement of the piston 806 in real-time.

In an embodiment, the tube housing the fiber optical sensor 828 is made from biocompatible materials such as medical-grade polymers, silicone, or titanium. These materials ensure compatibility with the human body and can be designed with grooves or channels to securely house the fiber optic cable. This design ensures that the fiber does not obstruct the piston's movement, maintaining the functionality of the device.

In an embodiment, the placement of the embedding of the fiber optic cable can vary depending on the specific design of the AIMD. One option is to run the fiber along the inner surface of the tube, either glued in place or secured in a groove. This positioning ensures that the fiber is properly aligned with the piston's path and is capable of detecting displacement with high precision. Alternatively, the fiber optic cable can be embedded inside the tube wall, enabling additional protection from external factors while ensuring that the fiber does not interfere with the piston's motion. In an embodiment, the fiber optic cable is embedded in the tube using one or more methods.

In an embodiment, one method of embedding the fiber optic cable is by machining grooves into the inner or outer surface of the tube. This technique ensures that the fiber is securely held in place and aligned with the piston, preventing mechanical damage. The grooves also maintain precise positioning, ensuring that the fiber is correctly integrated with the tube and does not interfere with the piston's motion.

In an embodiment, co-extrusion is used to embed the fiber optic cable during the extrusion process of the polymer tube. This method enables the integration of the fiber optic cable into the tube without significantly altering the tube's dimensions. The co-extrusion process embeds the fiber within the tube material, providing a strong and uniform bond while maintaining the structural integrity and form factor of the tube.

In an embodiment, adhesive bonding is utilized to embed the fiber optic cable into the tube. Medical-grade adhesives are used to bond the fiber directly to the inner wall of the tube. This method securely ensures that the fiber remains firmly in place during operation. The use of biocompatible adhesives ensures that the device remains safe for implantation.

In an embodiment, overmolding is employed to secure the fiber optic cable within the tube. In this process, a thin layer of polymer is molded around the fiber, providing additional protection, and creating a smooth, secure surface. The overmolding technique protects the fiber from external damage and ensures that the fiber remains securely in position during use, while also offering the benefit of a streamlined, uniform appearance.

In an embodiment, the tube is manufactured with integrated channels or lumens specifically designed to house the fiber optic cable. These channels are incorporated during the manufacturing process to ensure full functional clearance for the piston while providing protection for the fiber. This method prevents interference with the piston's movement, allowing for a smooth and uninterrupted operation of the device while securing the fiber in place.

If direct contact sensing is required, the fiber can be integrated with the piston itself. This integration comprises embedding the fiber within a channel inside the piston or attaching it to the outer surface. As the piston moves, it modulates the light path, enabling real-time displacement measurement.

For example, the piston is designed with a small central or side channel specifically intended for housing the fiber optic cable. The fiber is carefully inserted through this channel and secured using biocompatible adhesives, ensuring that the fiber remains well-protected while allowing the piston to move freely. This method helps maintain the structural integrity of the piston while providing secure housing for the fiber optic cable.

In an embodiment, the fiber optic cable is embedded directly into the piston material through an overmolding process. The fiber is placed within a mold, and the piston material, such as medical-grade polymer or silicone, is injected around it. This process keeps the fiber securely encased within the piston, maintaining the piston's structural integrity while providing a seamless and durable integration of the fiber optic cable.

In an embodiment, the fiber optic cable is attached to the outer surface of the piston. A small groove or recessed area is machined into the piston, and the fiber is placed inside the groove. The fiber is then secured using a biocompatible resin or adhesive. This method allows easier access for maintenance or replacement, while still providing a stable and secure attachment for the fiber optic cable.

In an additional embodiment, a coiled or flexible section of the fiber optic cable is integrated into the piston. This design allows the fiber to flex along with the piston's movement, minimizing stress and preventing wear on the fiber. The coiled design is particularly useful for ensuring continuous operation while accommodating the piston's range of motion.

Once the fiber is embedded in the tube or piston, the fiber optic sensor emits light through the fiber. As the piston moves, it alters the reflection or scattering of the light, which is then detected by the fiber optic system. The changes in light are processed and used to measure the piston's displacement.

Figure 8B:
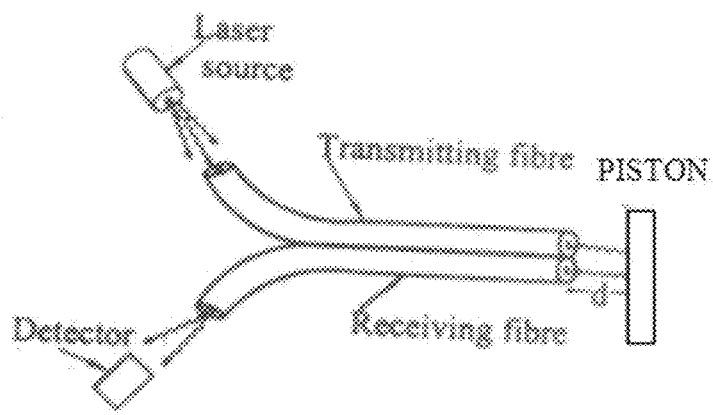
FIG. 8B illustrates a schematic diagram of the fiber optical sensor, according to one or more embodiments.

FIG. 8B illustrates a schematic diagram of the fiber optical sensor 828, according to one or more embodiments. The mechanism comprises a transmitting fiber and a reflecting fiber. The circuit is designed to detect the reflected light captured by the fiber optical sensor 828 and process it to generate a signal proportional to the piston's displacement. The received signal is amplified, and the changes in light properties (such as intensity or phase) are converted into a voltage or digital output. This output is directly correlated with the movement of the piston, enabling the measurement of its displacement within the tube.

Figure 8C:
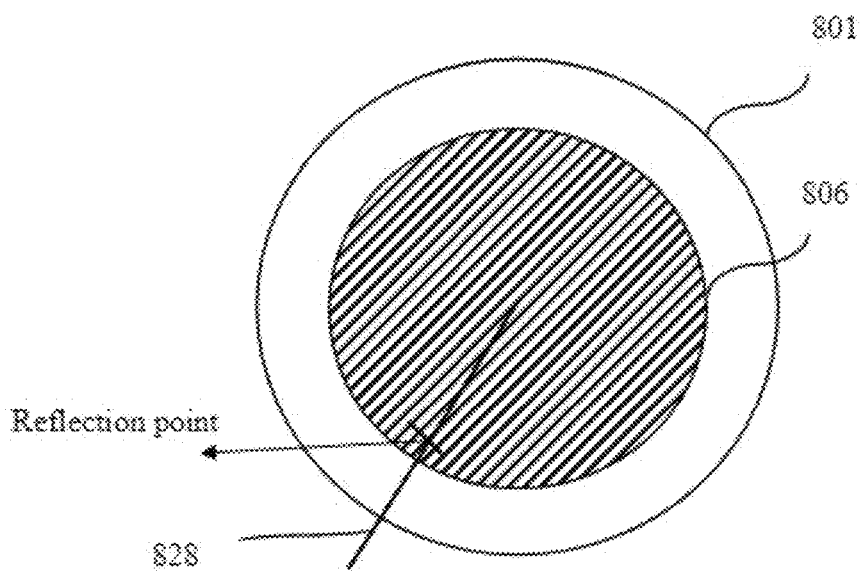
FIG. 8C illustrates the integration of the fiber optic sensing mechanism in a 4 mm diameter tube for measuring the displacement of the piston, according to one or more embodiments.

FIG. 8C illustrates the integration of the fiber optic sensing mechanism in a 4 mm diameter tube for measuring the displacement of the piston, according to one or more embodiments. In an embodiment, the active implantable medical device (AIMD) has a tubular structure. The tube is designed with an outer diameter of 4 mm, as illustrated in FIG. 8C and labelled as the 4 mm diameter tube 801. In FIG. 8C, the fiber optic sensor 828 is embedded alongside the inner wall of the tube or is connected directly to the piston. The fiber optic sensor 828 emits light that is directed toward predefined points within the device. As the piston moves within the tube, the fiber optic sensor 828 detects changes in the reflection or interference pattern of the light. The reflection point refers to a specific location where the light emitted by the fiber optic sensor 828 interacts with the piston or tube's surface and is reflected back to the sensor. This reflection is used to measure positional changes or displacement of the piston within the 4 mm diameter tube. The piston interacts with the fiber optic sensor 828 either directly, by reflecting light, or indirectly, by modulating the light path, ensuring continuous monitoring of its position within the tube.

Figure 9A:
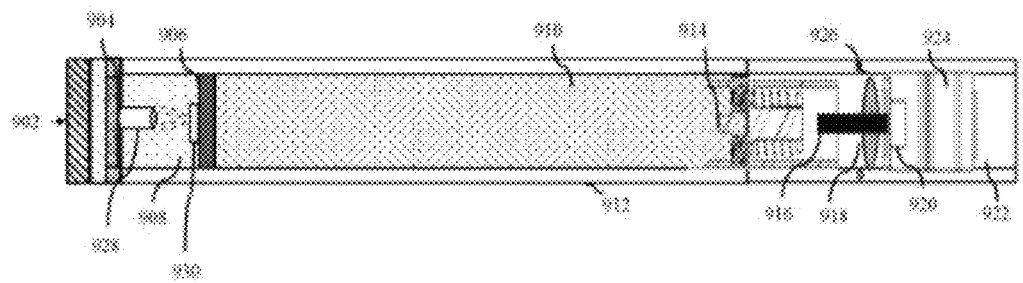
FIG. 9A is a schematic diagram illustrating a capacitance sensing mechanism for measuring the displacement of a piston in the active implantable medical device (AIMD), according to one or more embodiments.

FIG. 9A is a schematic diagram illustrating a capacitance sensing mechanism for measuring the displacement of a piston in the active implantable medical device (AIMD), according to one or more embodiments. The active implantable medical device (AIMD) comprises a semi-permeable membrane/plug 902, a sensor 904, a piston 906, an osmotic agent chamber 908, a drug chamber 910, casing 912, a relief valve 914, a push rod 916, a seal 918, an actuator 920, a battery 922, electronics 924, and a drug outlet 926. The function of these components has been explained above.

In an embodiment, the capacitance sensing mechanism operates using a capacitive displacement sensor. In an embodiment, the capacitance sensing mechanism operates using a capacitive proximity sensor. As shown in FIG. 9A, the capacitive displacement sensor operates by detecting changes in the capacitance between two electrodes such as a fixed plate 928 and a moving plate 930.

In an embodiment, the fixed plate 928 is embedded on the opposite side of the inner wall of the tube, while the moving plate 930 is attached to the piston 906. As the piston 906 moves within the tube, the dielectric material or distance between the fixed plate 928 and moving plate 930 changes, resulting in a variation in capacitance. A high-frequency alternating current (AC) signal is applied to the fixed plate 928. The use of high-frequency AC signals enhances the sensitivity of the device, enabling it to detect even small changes in capacitance. The choice of signal frequency is optimized to ensure minimal attenuation and interference while maintaining the displacement measurement.

Figure 9B:
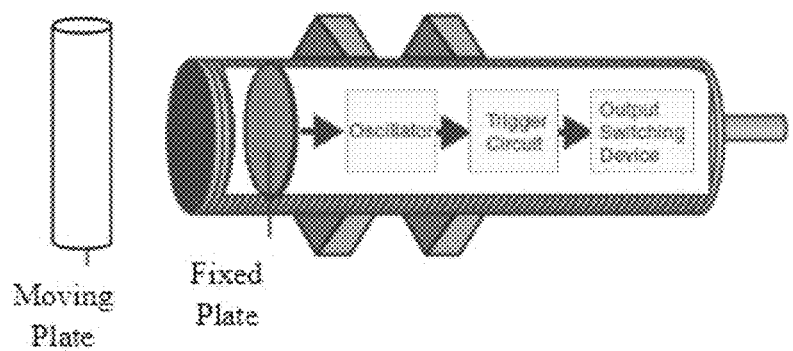
FIG. 9B shows a working principle of a capacitive displacement sensor for measuring the displacement of a piston in an AIMD, according to one or more embodiments.

FIG. 9B shows a working principle of a capacitive displacement sensor for measuring the displacement of a piston in an AIMD according to one or more embodiments. The diagram comprises a fixed plate embedded on the opposite side of the tube wall, a moving plate attached to the piston, an oscillator circuit, a trigger circuit, and an output switching device.

The fixed plate is stationary and positioned along the inner walls of the tube, while the moving plate, integrated with the piston, forms the second electrode of the capacitor. As the piston moves within the tube, the distance between the fixed plate and the moving plate changes, or the dielectric material between them is altered, causing variations in the capacitance.

The oscillator circuit generates a high-frequency alternating current (AC) signal applied to the fixed plate, creating an oscillating electric field between the two plates. Variations in capacitance caused by the piston's movement changes the characteristics of this oscillation. The trigger circuit monitors the output of the oscillator circuit to detect changes in the oscillation that correspond to variations in capacitance. It processes these signals and determines the piston's displacement by comparing them to predefined thresholds. The output switching device converts the processed signal into a digital signal, a control pulse, or another format required by the device, enabling tracking and integration into the AIMD's functionality.

Figure 9C:
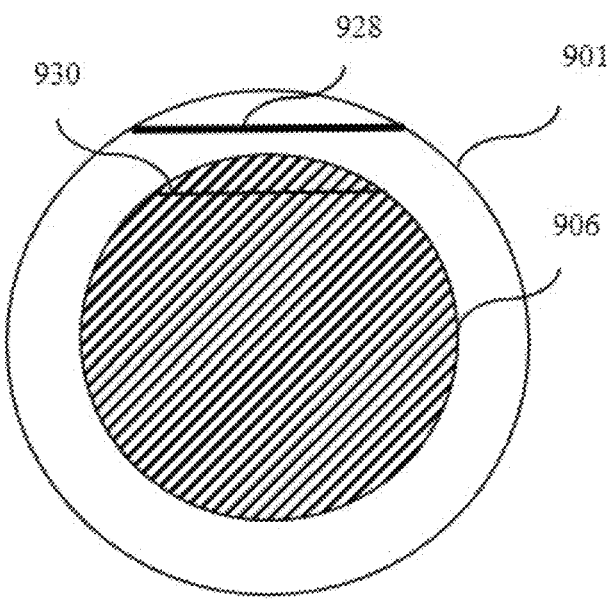
FIG. 9C illustrates the integration of the capacitive sensing mechanism in a 4 mm diameter tube for measuring the displacement of the piston, according to one or more embodiments.

FIG. 9C illustrates the integration of the capacitive sensing mechanism in a 4 mm diameter tube for measuring the displacement of the piston according to one or more embodiments. In an embodiment, the active implantable medical device (AIMD) has a tubular structure. The tube is designed with an outer diameter of 4 mm, as illustrated in FIG. 9C and labelled as the 4 mm diameter tube 901. In this embodiment, the fixed plate 928 is embedded on opposite sides of the tube wall, while a moving plate is attached directly to the piston 906. As the piston 906 moves, the relative distance between the fixed plate 928 and the moving plate 930 changes, altering the capacitance. This variation in capacitance is measured using a high-frequency alternating current (AC) signal applied to the fixed plate 928. The changes in capacitance are directly correlated to the piston's position, enabling the measurement of its displacement within the tube. This configuration allows for continuous monitoring of the piston's position while maintaining a compact design suitable for the 4 mm diameter tube.

Figure 10A:
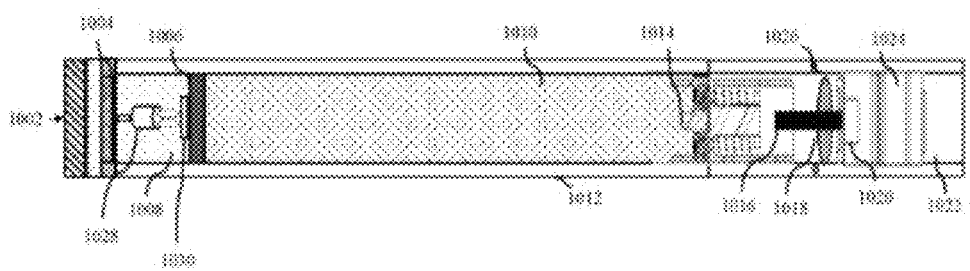
FIG. 10A is a schematic diagram illustrating an inductance sensing mechanism for measuring the displacement of a piston in the active implantable medical device (AIMD), according to one or more embodiments.

FIG. 10A is a schematic diagram illustrating an inductance sensing mechanism for measuring the displacement of a piston in the active implantable medical device (AIMD), according to one or more embodiments. The active implantable medical device (AIMD) comprises a semi-permeable membrane/plug 1002, a sensor 1004, a piston 1006, an osmotic agent chamber 1008, a drug chamber 1010, casing 1012, a relief valve 1014, a push rod 1016, a seal 1018, an actuator 1020, a battery 1022, electronics 1024, and a drug outlet 1026. The function of these components has been explained above.

In an embodiment, the inductance sensing mechanism operates using an inductive displacement sensor. In an embodiment, the inductance sensing mechanism operates using an inductive proximity sensor.

As shown in FIG. 10A, this sensor operates on the principles of inductance and eddy currents, leveraging changes in the magnetic coupling and permeability of the coil's magnetic field caused by the piston's movement. The sensor comprises the coil 1028, the oscillator and a conductive or magnetic material 1030 attached to the piston 1006 serves as the target.

When the coil 1028 is energized by the oscillator, it generates a high-frequency electromagnetic field. As the piston moves within this field, it affects the inductance of the coil 1028 by altering both the magnetic coupling and the effective permeability of the magnetic field. These changes are caused by the interaction between the magnetic field and the piston's material. Additionally, the motion of the conductive piston induces eddy currents, which result in energy losses and a reduction in the oscillation amplitude of the circuit.

The change in inductance caused by the piston's displacement is monitored by an external circuit, which provides the feedback on the piston's position. This displacement measurement is achieved by correlating the inductance variations to the piston's movement within the tube.

Figure 10B:
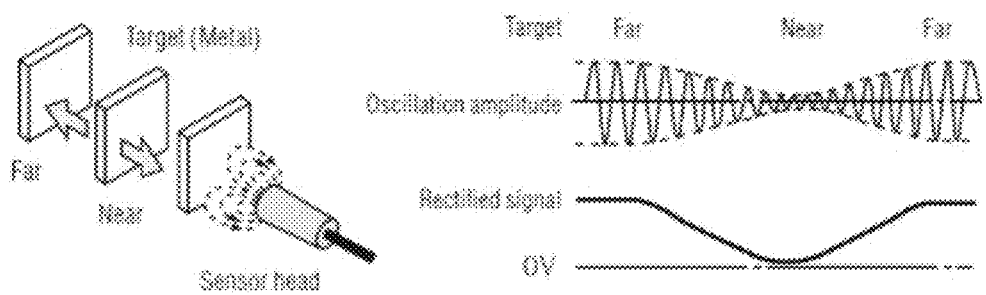
FIG. 10B shows a working principle of an inductive displacement sensor that operates using eddy current principles to measure the position of a piston, according to one or more embodiments.

FIG. 10B shows the working principle of an inductive displacement sensor that operates using eddy current principles to measure the position of a piston, according to one or more embodiments. The sensor may comprise an inductive coil, oscillator, amplitude detection, rectification, linearization circuit, and output processing components. The inductive coil, energized by a high-frequency alternating current (AC) signal from the oscillator, generates an electromagnetic field. As the piston, made of conductive or magnetic material, moves within this field, it induces eddy currents that increase energy loss. This results in a proportional reduction in the oscillation amplitude of the electromagnetic field. The amplitude is then rectified to convert the high-frequency AC signal into a direct current (DC) voltage that reflects the piston's position.

Figure 10C:
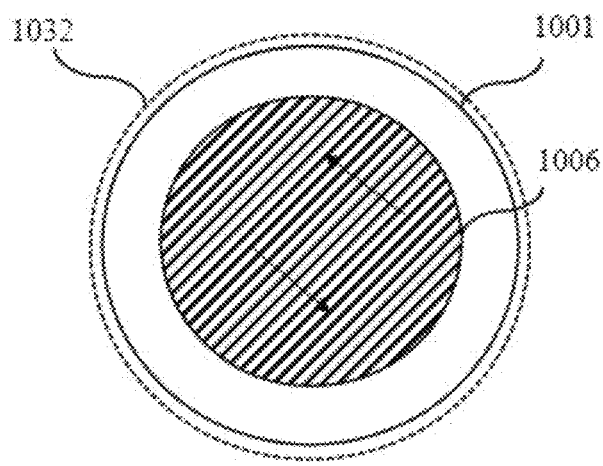
FIG. 10C illustrates the integration of an inductive sensing mechanism in a 4 mm diameter tube for measuring the displacement of a piston, according to one or more embodiments.

FIG. 10C illustrates the integration of an inductive sensing mechanism in a 4 mm diameter tube for measuring the displacement of a piston, according to one or more embodiments. In an embodiment, the active implantable medical device (AIMD) has a tubular structure. The tube is designed with an outer diameter of 4 mm, as illustrated in FIG. 10C and labelled as the 4 mm diameter tube 1001. In this embodiment, an inductive coil 1032 is wound around the tube. The inductive coil 1032 is wound around the tube with a casing such that it does not harm the body of the subject. The piston 1006, shown as a metallic or magnetic core, moves inside the tube. As the piston 1006 moves, it interacts with the magnetic field (indicated by arrows) generated by the inductive coil 1032, altering the inductance of the coil through changes in magnetic coupling and the effective permeability of the field. These variations in inductance are measured by external circuitry and are directly correlated to the piston's position, providing the displacement data.

Figure 11A:
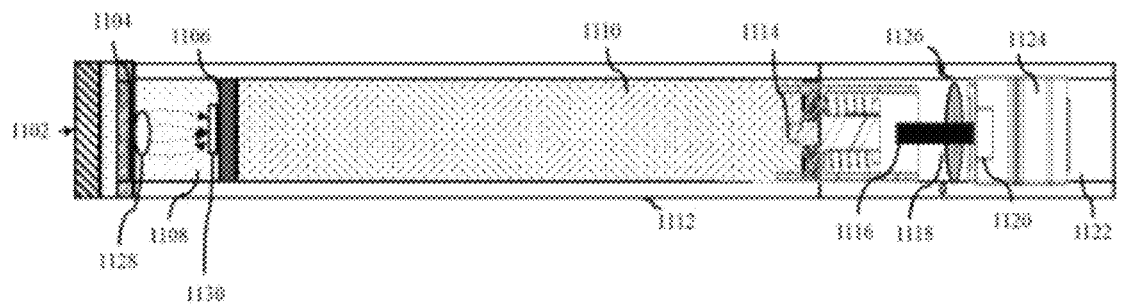
FIG. 11A is a schematic diagram illustrating an impedance sensing mechanism for measuring the displacement of a piston in the active implantable medical device (AIMD), according to one or more embodiments.

FIG. 11A is a schematic diagram illustrating an impedance sensing mechanism for measuring the displacement of a piston in the active implantable medical device (AIMD) according to one or more embodiments. The active implantable medical device (AIMD) comprises a semi-permeable membrane/plug 1102, a sensor 1104, a piston 1106, an osmotic agent chamber 1108, a drug chamber 1110, casing 1112, a relief valve 1114, a push rod 1116, a seal 1118, an actuator 1120, a battery 1122, electronics 1124, and a drug outlet 1126. The function of these components has been explained above.

In an embodiment, the impedance sensing mechanism operates using at least one of an inductive impedance sensor, a capacitive impedance sensor, an eddy current based impedance sensor, and a resonance-based impedance sensor. As shown in FIG. 11A, the eddy current based impedance sensor comprises a coil inside the sensor head 1128, which is driven by a high-frequency current from an oscillation circuit. This high-frequency current creates a magnetic field that induces eddy currents in the metallic measurement target 1130 (e.g., the inductive target attached to the piston) when it enters the magnetic field. As the piston moves, the relative position of the metallic measurement target 1130 changes within the high-frequency magnetic field. This change in position alters the eddy currents circulating in the target, which affects the impedance of the coil. The resulting change in impedance is directly proportional to the displacement of the piston. The sensor detects these impedance changes, and the system processes the resulting oscillations to determine the distance or displacement of the piston within the device. The impedance sensing mechanism functions in such a way ensuring that the system operates without adversely affecting the human body. The AIMD may comprise biocompatible and non-toxic materials, and anti-biofouling coatings (e.g., hydrophilic polymers or diamond-like carbon) to prevent tissue adhesion, inflammation, or degradation over time. The device may be designed to operate with low current level, and low voltage level without affecting the subject. The device is ensured to have proper insulation to prevent leakage currents.

Figure 11B:
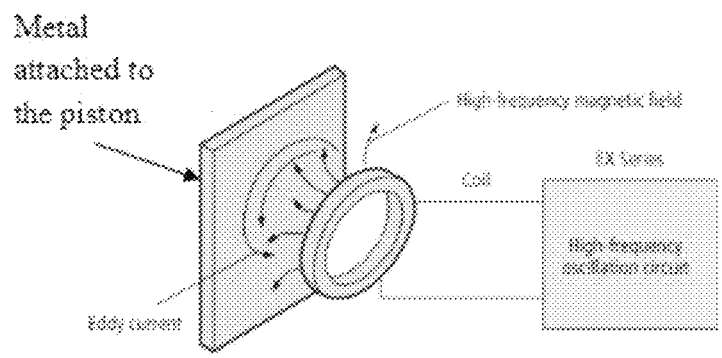
FIG. 11B shows a working principle of the eddy current impedance sensor for measuring the displacement of a piston in an AIMD, according to one or more embodiments.

FIG. 11B shows the working principle of the eddy current impedance sensor for measuring the displacement of a piston in an AIMD, according to one or more embodiments. The diagram shows how the oscillation circuit drives a high-frequency current through the coil inside the sensor head, creating a magnetic field. The measurement target (attached to the piston) induces eddy currents in the field, which causes a change in the impedance of the coil. The circuit detects these impedance variations and converts them into an electrical signal, which is proportional to the displacement of the piston.

Figure 11C:
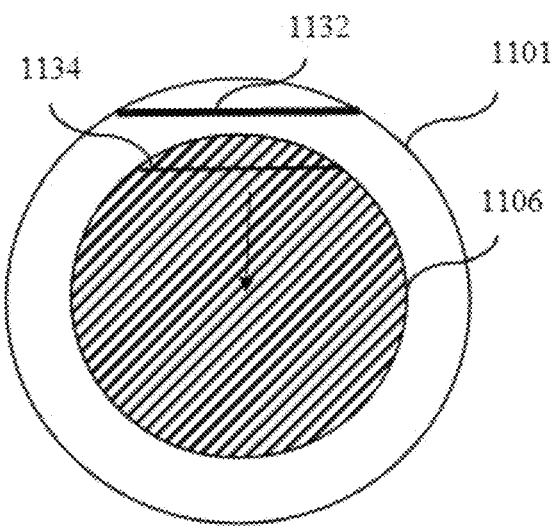
FIG. 11C illustrates an impedance sensing mechanism integrated into a 4 mm diameter tube for measuring the displacement of a piston, according to one or more embodiments.

FIG. 11C illustrates an impedance sensing mechanism integrated into a 4 mm diameter tube for measuring the displacement of a piston, according to one or more embodiments. In an embodiment, the active implantable medical device (AIMD) has a tubular structure. The tube is designed with an outer diameter of 4 mm, as illustrated in FIG. 11C and labelled as the 4 mm diameter tube 1101. This design comprises a fixed electrode 1132 mounted on the inner wall of the tube and a moving electrode 1134 attached to the piston 1106.

As the piston moves, the distance between the fixed and moving electrodes changes, as does the material between them (e.g., air, fluid, or the piston's material). These variations influence the impedance, which depends on factors like the dielectric properties of the medium and the distance between the electrodes. Impedance is inversely proportional to the effective surface area and the permittivity of the medium between the electrodes. When an alternating current (indicated by an arrow) flows through the electrodes, the resulting impedance variations are measured and correlated to the piston's displacement.

Figure 12A:
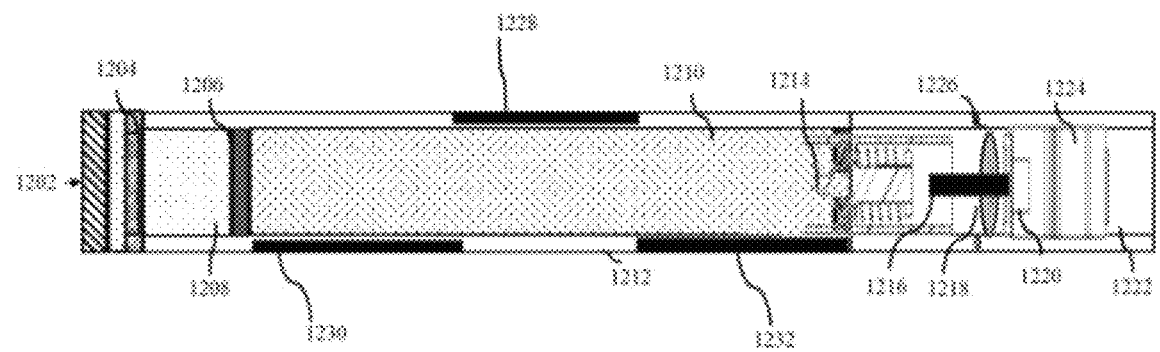
FIG. 12A shows a schematic diagram illustrating an implantable medical device (AIMD) that comprises a Linear Variable Differential Transformer (LVDT) used for measuring the displacement of a piston, according to one or more embodiments.

FIG. 12A illustrates a schematic diagram of an implantable medical device (AIMD) that comprises a Linear Variable Differential Transformer (LVDT) used for measuring the displacement of a piston according to one or more embodiments. The active implantable medical device (AIMD) comprises a semi-permeable membrane/plug 1202, a sensor 1204, a piston 1206, an osmotic agent chamber 1208, a drug chamber 1210, casing 1212, a relief valve 1214, a push rod 1216, a seal 1218, an actuator 1220, a battery 1222, electronics 1224, and a drug outlet 1226. The function of these components has been explained above.

The LVDT comprises a primary winding 1228, two secondary windings (S1 and S2) 1230 and 1232, and a core. In an embodiment, the core is physically attached to the piston 1206, which moves longitudinally within the active implantable medical device (AIMD) in response to the osmotic pressure. In an embodiment, the coil sizes are fabricated using advanced micro-coil techniques, with the primary winding 1228 typically having a diameter range of 1-2 mm, and the secondary windings (S1 and S2) 1230 and 1232 ranging from 1-1.5 mm in diameter. These dimensions ensure the LVDT can be embedded within the small dimensions of the AIMD while still maintaining its functionality. In an embodiment, the core, made of a biocompatible magnetic material, is typically around 1-1.5 mm in length and 0.5-1 mm in diameter, ensuring that it moves smoothly within the winding coils as the piston shifts.

In this configuration, the primary winding 1228 is energized with an alternating current (AC) signal, creating a magnetic field within the core. The secondary windings (S1 and S2) 1230 and 1232 are symmetrically arranged on either side of the primary winding 1228. As the piston 1206 moves (e.g., from left to right), the core moves within the windings, altering the position of the core relative to the primary and secondary windings.

When the core is positioned at the far left or right end (as the piston 1206 starts its movement), the distribution of the magnetic field is unequal between the secondary windings 1230 and 1232. This induces a voltage difference in the secondary windings 1230 and 1232, which is proportional to the amount of displacement. As the piston 1206 moves towards the opposite end, the core shifts within the windings, and the voltage difference in the secondary windings 1230 and 1232 changes accordingly. When the core reaches a central position (the midpoint of the windings), the magnetic flux is evenly distributed, and the induced voltages in both secondary windings 1230 and 1232 are equal.

In an embodiment, the components of the LVDT, including the primary and secondary windings and the core, need to be fabricated using advanced micro-coil techniques to achieve the small dimensions necessary for the AIMD. For example, micro-coil winding technology can produce coils with diameters in the range of 1-2 mm for the primary winding and 1-1.5 mm for the secondary windings, which would fit within the limited space available. These coils can be fabricated using techniques such as laser micromachining or photolithography, that enables construction of small-scale components while preserving their electrical properties.

The core can be manufactured using micro-milling or electroforming processes to achieve the required size and magnetic properties while ensuring smooth movement within the winding coils. The dimensions of the core, typically around 1-1.5 mm in length and 0.5-1 mm in diameter, can be fabricated with high precision to ensure compatibility with the miniature dimensions of the device. To further optimize the LVDT for use in a 4 mm implantable device, thin-film technology can be employed. This enables the creation of ultra-thin, flexible coils that can be integrated into the structure of the device without compromising space or functionality. The use of flexible substrates, such as polyimide or other biocompatible polymers, ensures that the LVDT's components remain durable and functional within the environment of the body.

Further, packaging and integration methods are used to ensure that the LVDT and its components are securely housed within the device while maintaining its biocompatibility. Advanced 3D packaging or micro-assembly techniques can be used to integrate the LVDT components into the device's compact form. These methods enable positioning of the components and ensure the proper alignment of the core and windings.

Figure 12B:
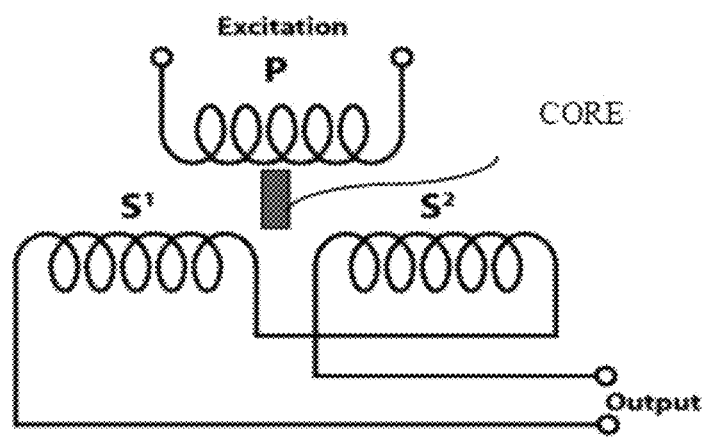
FIG. 12B shows the working principle of the Linear Variable Differential Transformer (LVDT), according to one or more embodiments.

FIG. 12B shows the working principle of the Linear Variable Differential Transformer (LVDT), according to one or more embodiments. The LVDT is designed to measure the voltage difference between the two secondary windings (S1 and S2) of the LVDT and generate an output signal that is proportional to the displacement of the piston. The circuit comprises an excitation signal source that supplies an alternating current (AC) to the primary winding. This AC signal creates a magnetic field within the core of the LVDT. The core, which is attached to the piston, moves within the primary and secondary windings as the piston shifts. This movement causes a change in the distribution of the magnetic field, which in turn induces voltages in the two secondary coils (S1 and S2).

The voltage difference between the secondary windings is detected and processed by the signal processing unit. The circuit amplifies the voltage difference and converts it into a usable output signal. This output signal, typically a voltage or current, is proportional to the piston's displacement. In some embodiments, the output signal from the LVDT circuit can be used directly to control the valve module, thereby regulating the one-way flow of the drug based on the displacement of the piston.

Figure 13A:
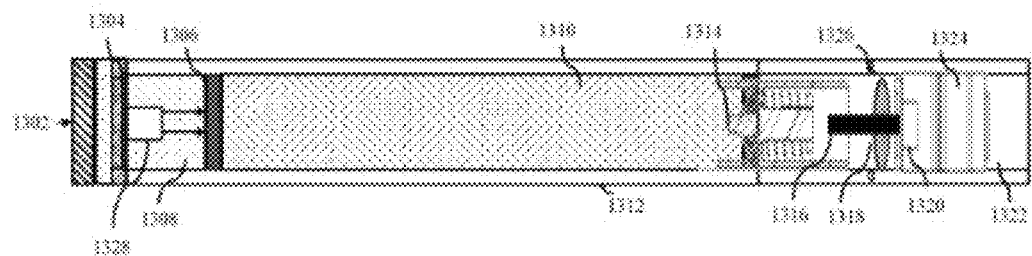
FIG. 13A is a schematic diagram illustrating an implantable medical device (AIMD) that comprises an ultrasonic sensor for measuring the displacement of a piston in an implantable medical device (AIMD), according to one or more embodiments.

FIG. 13A illustrates a schematic diagram illustrating an implantable medical device (AIMD) that comprises an ultrasonic sensor for measuring the displacement of a piston in an implantable medical device (AIMD), according to one or more embodiments. The active implantable medical device (AIMD) comprises a semi-permeable membrane/plug 1302, a sensor 1304, a piston 1306, an osmotic agent chamber 1308, a drug chamber 1310, casing 1312, a relief valve 1314, a push rod 1316, a seal 1318, an actuator 1320, a battery 1322, electronics 1324, and a drug outlet 1326. The function of these components has been explained above.

The ultrasonic sensor 1328 comprises an ultrasonic transducer, which serves both as the emitter and receiver of ultrasonic waves. The transducer emits a short ultrasonic pulse from the sensor head, which travels through the surrounding medium (typically air or another fluid) toward the piston.

Once the ultrasonic wave encounters the piston, it is reflected back toward the sensor. The time-of-flight (ToF), or the time taken for the pulse to travel from the sensor to the piston and back, is recorded by the ultrasonic transducer. This time measurement (T) is used for calculating the distance (L) between the sensor and the piston. Using the known sonic speed (C) in the medium, the distance is calculated by the following formula:

$$\text{Distance } L = \tfrac{1}{2} \times T \times C$$

Here, L represents the distance to the piston, T is the time interval between emission and reception of the wave, and C is the known speed of sound in the medium through which the wave travels. The factor of ½ is used because T represents the round-trip travel time of the wave, from the sensor to the piston and back. By measuring this distance in real-time, the ultrasonic sensor 1328 enables monitoring the piston's displacement within the device.

Figure 13B:
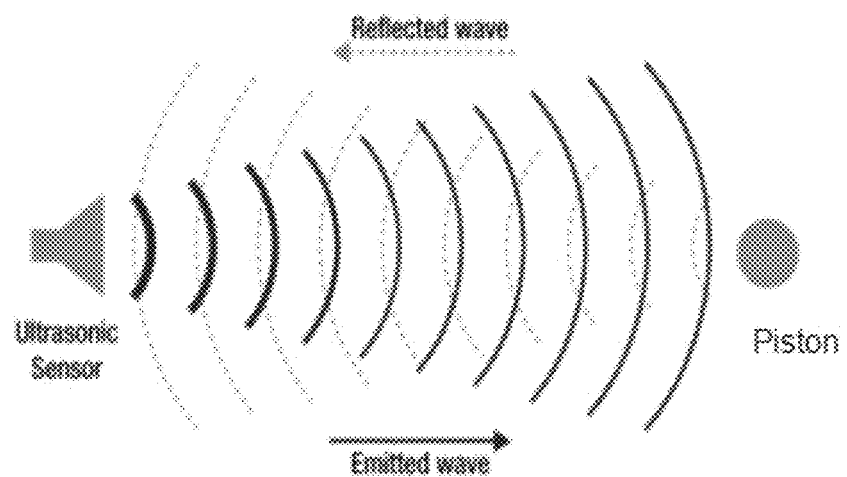
FIG. 13B shows a working principle of the ultrasonic sensor, according to one or more embodiments.

FIG. 13B shows the working principle of the ultrasonic sensor, according to one or more embodiments. In FIG. 13B, the ultrasonic sensor emits the ultrasonic waves using an oscillator, which travels through the medium and reflects off the piston. Upon receiving the reflected signal, the ultrasonic sensor detects the ToF, which is processed by a signal processing unit. The ultrasonic sensor calculates the displacement of the piston based on the ToF and the known speed of sound in the medium using a signal processing unit. The calculated displacement is then converted into an output signal by the output circuit, which provides the measurement in either analog or digital form.

To integrate the ultrasonic sensor into a 4 mm implantable device, MEMS (Micro-Electro-Mechanical Systems) technology is used. MEMS-based transducers, such as Capacitive Micromachined Ultrasonic Transducers (CMUTs), are smaller and consume significantly less power compared to traditional piezoelectric transducers. Their compact size and compatibility with integrated circuits make them highly suitable for space-constrained implantable devices.

In an embodiment, custom-designed ASICs (Application-Specific Integrated Circuit) integrate functions such as signal generation, processing, and output into a single chip. This reduces the overall size of the electronic components, enhances energy efficiency, and simplifies system-level integration.

Figure 14:
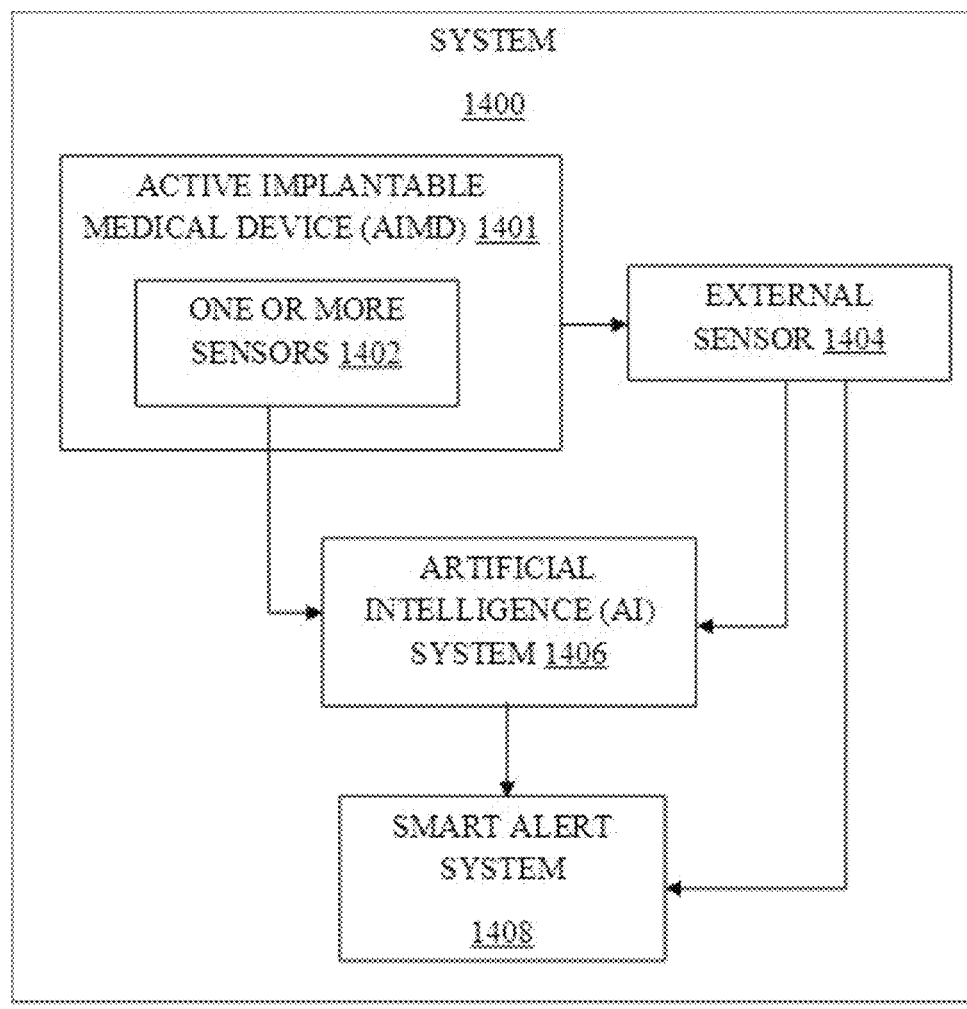
FIG. 14 illustrates a system, according to one or more embodiments.

FIG. 14 illustrates a system 1400 according to one or more embodiments. The system 1400 comprises one or more sensors 1402, an external sensor 1404, an artificial intelligence (AI) system 1406 and a smart alert system 1408. The one or more sensors 1402 configured to measure a displacement of a piston and provide displacement data during real-time operation of an active implantable medical device (AIMD) 1401. The external sensor 1404 is configured to provide a physiological parameter of a user having the active implantable medical device (AIMD) 1401. The external sensor 1404 may be placed outside the active implantable medical device (AIMD) 1401. The artificial intelligence (AI) system 1406 is configured to receive and analyze the displacement data and the physiological parameter to predict a body response of the user using the active implantable medical device (AIMD) 1401. The AI system 1406 and the active implantable medical device (AIMD) 1401 may be in wireless communication with one another. The AI system 1406 may be configured to store monitored inputs from the active implantable medical device (AIMD) 1401 and the physiological parameter of the user. In an embodiment, the AI system 1406 implements one or more of predictive learning, machine learning, automated planning and scheduling, machine perception, computer vision and affective computing to predict the body response of the user. The AI system 1406 may be configured to access a medication schedule and to send a signal to administer medicine based on the medication schedule to the active implantable medical device (AIMD) 1401.

The smart alert system 1408 is in communication with the active implantable medical device (AIMD) 1401 and the external sensor 1404 is configured to proactively send out a signal for help based on a predicted body response by the AI system 1406. The system 1400 is configured to update a machine learning model based on a physical parameter of the active implantable medical device (AIMD) 1401 and a generated physiological condition of the user on a real-time basis. The system 1400 may be configured to adjust a drug dosing schedule based on a predicted outcome of AI. The AI system 1406 may be configured to predict a future working condition of the active implantable medical device (AIMD) 1401 and notify the user or a healthcare provider, if the future working condition of the active implantable medical device (AIMD) 1401 is not within ±15% value of corresponding expected value of the active implantable medical device (AIMD) 1401. The future working condition comprises the displacement of the piston and an osmotic pressure of the active implantable medical device (AIMD) 1401.

Figure 15:
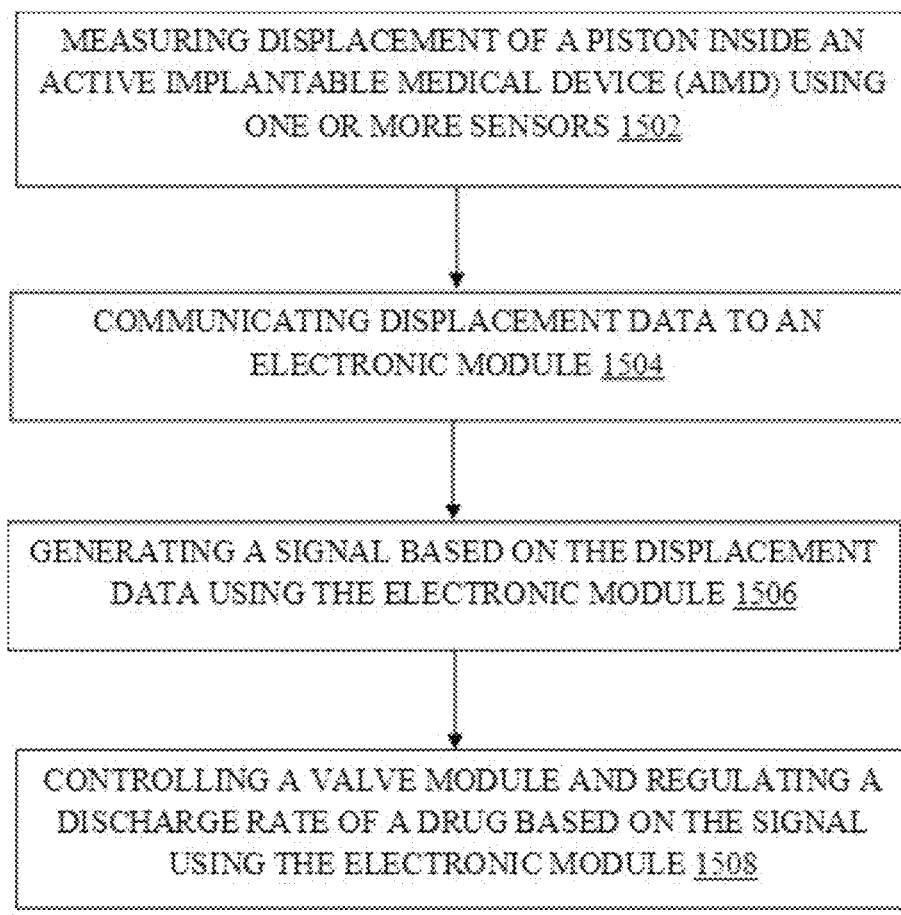
FIG. 15 illustrates a method, according to one or more embodiments.

FIG. 15 illustrates a method according to one or more embodiments. The method comprises the following technical steps: measuring displacement of a piston inside an active implantable medical device (AIMD) using one or more sensors (at step 1502); communicating displacement data to an electronic module (at step 1504); generating a signal based on the displacement data using the electronic module (at step 1506); and controlling a valve module and regulating a discharge rate of a drug based on the signal using the electronic module (at step 1508). The displacement of the piston corresponds to the discharge rate of the drug from the active implantable medical device (AIMD).

The displacement of the piston as a function of osmotic pressure w may be calculated as $$\text{DISPLACEMENT } D = \frac{2CRT}{A}\left(\frac{1}{\pi 2} - \frac{1}{\pi 1}\right) \quad \text{Equation (I)}$$

where R is ideal gas constant, T is temperature, C is concentration of an osmotic agent, A is cross sectional area, $\pi 1$ is initial osmotic pressure and $\pi_2$ is current osmotic pressure.

The active implantable medical device (AIMD) may be configured to use machine learning to adjust a drug dose as per the need of a user. The one or more sensors may be positioned external to the active implantable medical device (AIMD). The one or more sensors may be positioned internally to the active implantable medical device (AIMD).

Figure 16:
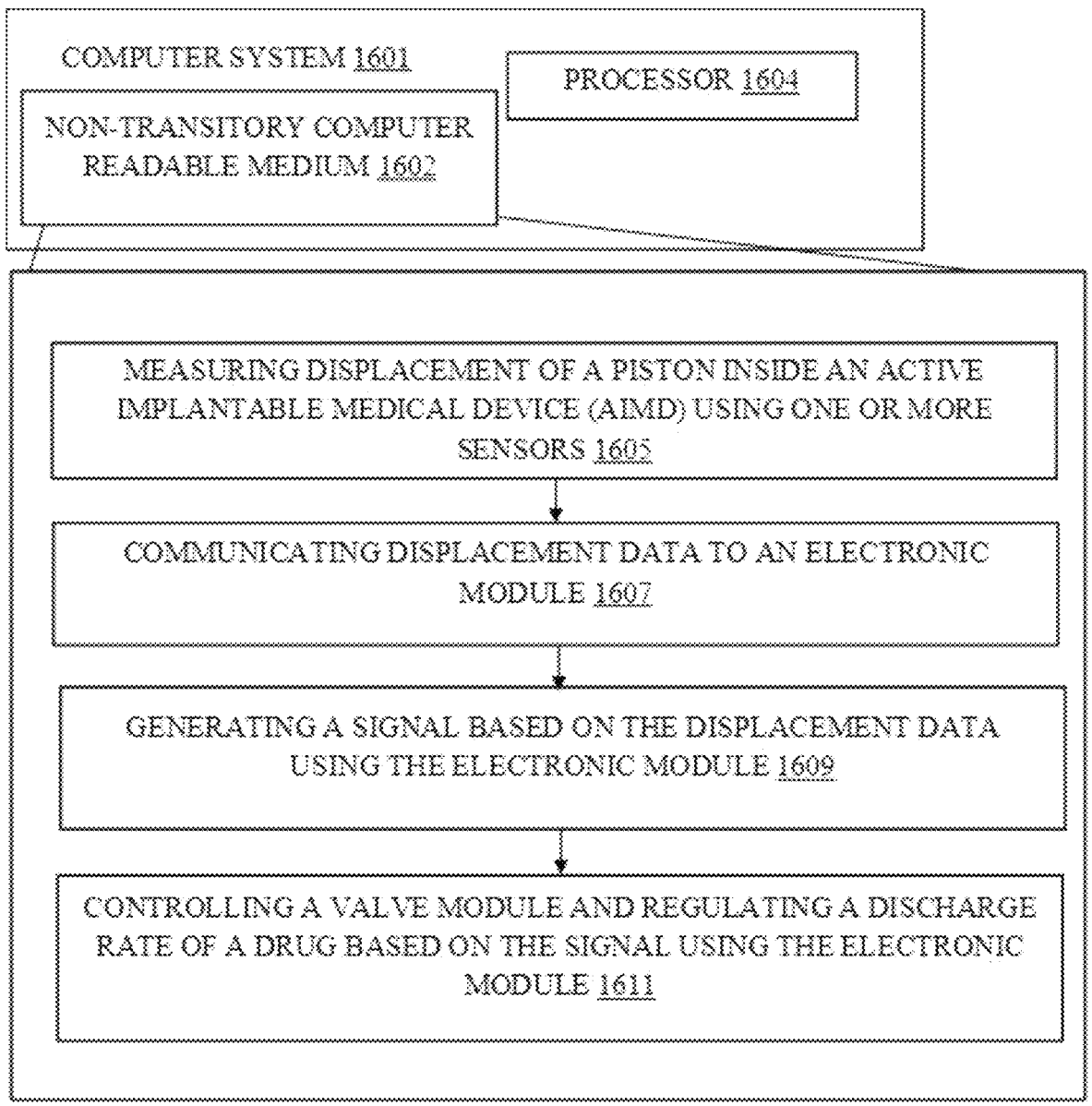
FIG. 16 illustrates a non-transitory computer readable storage medium, according to one or more embodiments.

FIG. 16 illustrates a non-transitory computer readable storage medium, according to one or more embodiments. According to an embodiment, disclosed is a computer system 1601 comprising the non-transitory computer readable storage medium 1602 having stored thereon instructions executable by a processor 1604 to perform operations comprising: measuring displacement of a piston inside an active implantable medical device (AIMD) using one or more sensors (at step 1605); communicating displacement data to an electronic module (at step 1607); generating a signal based on the displacement data using the electronic module (at step 1609); and controlling a valve module and regulating a discharge rate of a drug based on the signal using the electronic module (at step 1611). The displacement of the piston corresponds to the discharge rate of the drug from the active implantable medical device (AIMD).

The displacement of the piston as a function of osmotic pressure if may be calculated as $$\text{DISPLACEMENT } D = \frac{2CRT}{A}\left(\frac{1}{\pi 2} - \frac{1}{\pi 1}\right) \quad \text{Equation (I)}$$

where R is ideal gas constant, T is temperature, C is concentration of an osmotic agent, A is cross sectional area, $\pi 1$ is initial osmotic pressure and $\pi_2$ is current osmotic pressure.

The active implantable medical device (AIMD) may be configured to use machine learning to adjust a drug dose as per the need of a user. The one or more sensors may be positioned external to the active implantable medical device (AIMD). The one or more sensors may be positioned internally to the active implantable medical device (AIMD).

Industrial Applicability: The active implantable medical device (AIMD) has industrial applicability in the fields of healthcare and medical technology, particularly for drug delivery systems. The active implantable medical device (AIMD) can be used to manage chronic conditions, such as diabetes, hypertension, and hormonal imbalances, where precise and consistent medication dosing is critical. The device is also applicable for controlled opioid administration, addressing the challenges of substance abuse and overdose prevention. The AIMD's real-time monitoring and adjustment capabilities make it valuable for personalized medicine, enabling tailored drug regimens based on individual patient needs. Further, its compact design and ability to function as a subcutaneous implant make it suitable for long-term use in various healthcare settings, including outpatient and home care. Its adaptability to integrate advanced technologies such as machine learning for optimizing dosing schedules enhances its relevance in modern medical applications, contributing to improved patient outcomes and reducing healthcare costs.

It should be noted that the flowchart and the suggested time limits and parameters are meant to be exemplary, and that there could be other measures or criteria used in order to maximize safety and accuracy.

REFERENCE SIGNS LIST 202, 702, 802, 902, 1002, 1102, 1202, 1302—Semi-permeable membrane/plug
204, 704, 804, 904, 1004, 1104, 1204, 1304—Sensor
206, 706, 806, 906, 1006, 1106, 1206, 1306—Piston
208, 708, 808, 908, 1008, 1108, 1208, 1308—Osmotic agent chamber
210, 710, 810, 910, 1010, 1110, 1210, 1310—Drug chamber
212, 304, 602, 712, 812, 912, 1012, 1112, 1212, 1312—Casing
214, 714, 814, 914, 1014, 1114, 1214, 1314—Relief valve
216, 716, 816, 916, 1016, 1116, 1216, 1316—Pushrod
218, 718, 818, 918, 1018, 1118, 1218, 1318—Seal
220, 610, 720, 820, 920, 1020, 1120, 1220, 1320—Actuator
222, 722, 822, 922, 1022, 1122, 1222, 1322—Battery
224, 724, 824, 924, 1024, 1124, 1224, 1324—Electronics
226, 608, 726, 826, 926, 1026, 1126, 1226, 1326—Drug outlet
300—Hollow fiber membrane
302—Flexible fibers
306—Second end
612—Needle-like structure
614—Vibrating plate
616—Ball-like structure
701—4 mm diameter tube
728—Small biocompatible magnet
730, 732—External magnetic sensor
734A, 734B and 734C—One or more small magnets
736A and 736B—Set of external magnetic sensors
738—Gradient field sensor
740—Gradient field
801—4 mm diameter tube
828—Fiber optical sensor
901—4 mm diameter tube
928—Fixed plate
930—Moving plate
1001—4 mm diameter tube
1028—Coil
1030—Conductive or magnetic material
1032—Inductive coil
1101—4 mm diameter tube
1128—Sensor head
1130—Metallic measurement target
1132—Fixed electrode
1134—Moving electrode
1228—Primary winding
1230, 1232—Secondary windings
1328—Ultrasonic sensor
1400—System
1401—Active implantable medical device (AIMD)
1402—One or more sensors
1404—External sensor
1406—Artificial intelligence (AI) system
1408—Smart alert system
1502, 1504, 1506, 1508—Method steps
1601—Computer system
1602—Non-transitory computer readable medium
1604—Processor
1605, 1607, 1609, 1610—Method steps

What is claimed is:

1. An active implantable medical device (AIMD), comprising:
 a permeability module that allows ingress flow of a fluid to an osmotic agent chamber and generates osmotic pressure;
 a piston that moves longitudinally within the active implantable medical device (AIMD) in response to the osmotic pressure;
 a drug chamber that comprises a drug and a valve module to allow one-way flow of the drug from the drug chamber to outside the active implantable medical device (AIMD);
 a sensor module configured to measure a displacement of the piston and provide displacement data during real-time operation of the active implantable medical device (AIMD);
 an electronic module that communicates a signal to the valve module to control the valve module and regulate the one-way flow of the drug based on the displacement data of the piston such that a dose-to-dose drug ejection variation from the active implantable medical device (AIMD) is less than ±25% by volume of a predetermined volume; and
 a machine learning, model configured to cause the active implantable medical device (AIMD) to trigger an alert in case dosing is outside threshold limits.

2. The active implantable medical device (AIMD) of claim 1, wherein the sensor module comprises one or more non-pressure-based sensors.

3. The active implantable medical device (AIMD) of claim 2, wherein the one or more non-pressure-based sensors comprise at least one of a Linear Variable Differential Transformer (LVDT), a magnetic position sensor, an optical sensor, an ultrasonic sensor, a capacitive displacement sensor, an inductive displacement sensor, a capacitive proximity sensor, an inductive proximity sensor, an inductive impedance sensor, a capacitive impedance sensor, an eddy current based impedance sensor, and a resonance-based impedance sensor.

4. The active implantable medical device (AIMD) of claim 1, wherein the electronic module comprises a microcontroller.

5. The active implantable medical device (AIMD) of claim 1, wherein the drug chamber comprises a threshold displacement limit that corresponds to a prescribed drug quantity.

6. The active implantable medical device (AIMD) of claim 5, wherein the prescribed drug quantity is a maximum drug quantity intended for a subject.

7. The active implantable medical device (AIMD) of claim 1, wherein the displacement of the piston is proportional to an amount of discharge of drug.

8. The active implantable medical device (AIMD) of claim 1, wherein the displacement of the piston and an osmotic pressure within the permeability module has a correlation.

9. The active implantable medical device (AIMD) of claim 1, wherein the active implantable medical device (AIMD) is activated to start operation either manually or automatically.

10. The active implantable medical device (AIMD) of claim 1, wherein the valve module comprises a flow switch.

11. The active implantable medical device (AIMD) of claim 1, wherein an amount of drug released in a single shot of the active implantable medical device (AIMD) equals a distance travelled by the piston times cross sectional area of the active implantable medical device (AIMD).

12. The active implantable medical device (AIMD) of claim 1, wherein the dose-to-dose drug ejection variation is ±10% or less by the predetermined volume.

13. The active implantable medical device (AIMD) of claim 1, wherein the sensor module comprises a non-pressure sensor.

14. A method, comprising:
measuring displacement of a piston inside an active implantable medical device (AIMD) using one or more sensors, wherein the active implantable medical device (AIMD) comprises a permeability module that allows ingress flow of a fluid to an osmotic agent chamber and generates osmotic pressure;
communicating displacement data during real-time operation of the active implantable medical device (AIMD) to an electronic module such that a dose-to-dose drug ejection variation from the active implantable medical device (AIMD) is less than ±25% by volume of a predetermined volume;
generating a signal based on the displacement data using the electronic module; and
controlling a valve module and regulating a discharge rate of a drug based on the signal using the electronic module,
wherein the displacement of the piston corresponds to the discharge rate of the drug from the active implantable medical device (AIMD).

15. The method of claim 14, wherein the displacement of the piston as a function of osmotic pressure π is calculated as $$\text{DISPLACEMENT } D = \frac{2CRT}{A}\left(\frac{1}{\pi 2} - \frac{1}{\pi 1}\right)$$

wherein R is ideal gas constant, T is temperature, C is concentration of an osmotic agent, A is cross sectional area, $\pi 1$ is initial osmotic pressure and $\pi_2$ is current osmotic pressure.

16. The method of claim 14, wherein the active implantable medical device (AIMD) is configured to use a machine learning model to adjust a drug dose as per need of a user.

17. A non-transitory computer readable storage medium comprising sequence of instructions, which when executed by a processor causes:
measuring displacement of a piston inside an active implantable medical device (AIMD) using one or more sensors, wherein the active implantable medical device (AIMD) comprises a permeability module that allows ingress flow of a fluid to an osmotic agent chamber and generates osmotic pressure;
communicating displacement data during real-time operation of the active implantable medical device (AIMD) to an electronic module such that a dose-to-dose drug ejection variation from the active implantable medical device (AIMD) is less than ±25% by volume of a predetermined volume;
generating a signal based on the displacement data using the electronic module; and
controlling a valve module and regulating a discharge rate of a drug based on the signal using the electronic module,
wherein the displacement of the piston corresponds to the discharge rate of the drug from the active implantable medical device (AIMD).

18. The non-transitory computer readable storage medium of claim 17, wherein the displacement of the piston as a function of osmotic pressure π is calculated as $$\text{DISPLACEMENT } D = \frac{2CRT}{A}\left(\frac{1}{\pi 2} - \frac{1}{\pi 1}\right)$$

wherein R is ideal gas constant, T is temperature, C is concentration of an osmotic agent, A is cross sectional area, $\pi 1$ is initial osmotic pressure and $\pi_2$ is current osmotic pressure.

19. The non-transitory computer readable storage medium of claim 17, wherein the active implantable medical device (AIMD) is configured to use a machine learning model to adjust a drug dose as per need of a user.

20. The non-transitory computer readable storage medium of claim 17, wherein the one or more sensors are external to the active implantable medical device (AIMD).

* * * * *